US012594257B2

(12) United States Patent
Hill Mongabure et al.

(10) Patent No.: US 12,594,257 B2
(45) Date of Patent: Apr. 7, 2026

(54) MEANS AND METHODS FOR IMPROVING ANTI-TUMORAL EFFICACY OF TRANSMEMBRANE CHANNEL PROTEIN BLOCKERS

(71) Applicants: ARDAN PHARMA S.A.S., Buenos Aires (AR); UNIVERSIDAD DE LA REPÚBLICA ORIENTAL DEL URUGUAY, Montevideo (UY); INSTITUT PASTEUR DE MONTEVIDEO, Montevideo (UY)

(72) Inventors: Marcelo Rafael Hill Mongabure, Canelones (UY); Mercedes Segovia, Canelones (UY); Helena Pardo Minetti, Montevideo (UY); Álvaro Mombrú, Montevideo (UY); Sabina Victoria, Tübingen (DE); Analia Castro, Montevideo (UY); Maria Inés Varela Vega, Sunchales Santa Fe (AR)

(73) Assignees: ARDAN PHARMA S.A.S., Buenos Aires (AR); UNIVERSIDAD DE LA REPÚBLICA ORIENTAL DEL URUGUAY, Montevideo (UY); INSTITUT PASTEUR DE MONTEVIDEO, Montevideo (UY)

( * ) Notice: Subject to any disclaimer, the term of this patent is extended or adjusted under 35 U.S.C. 154(b) by 258 days.

(21) Appl. No.: 18/565,865

(22) PCT Filed: Jun. 2, 2022

(86) PCT No.: PCT/IL2022/050587
§ 371 (c)(1),
(2) Date: Nov. 30, 2023

(87) PCT Pub. No.: WO2022/254442
PCT Pub. Date: Dec. 8, 2022

(65) Prior Publication Data
US 2024/0148687 A1 May 9, 2024

Related U.S. Application Data

(60) Provisional application No. 63/196,260, filed on Jun. 3, 2021.

(51) Int. Cl.
| | |
|---|---|
| *A61P 35/00* | (2006.01) |
| *A61K 9/51* | (2006.01) |
| *A61K 31/138* | (2006.01) |
| *A61K 31/166* | (2006.01) |
| *A61K 31/167* | (2006.01) |
| *A61K 31/352* | (2006.01) |
| *C07D 211/84* | (2006.01) |

(52) U.S. Cl.
CPC .......... *A61K 31/352* (2013.01); *A61K 9/5161* (2013.01); *A61K 31/138* (2013.01); *A61K 31/166* (2013.01); *A61K 31/167* (2013.01); *A61P 35/00* (2018.01)

(58) Field of Classification Search
None
See application file for complete search history.

(56) References Cited

U.S. PATENT DOCUMENTS

2022/0184004 A1    6/2022  Hill Mongabure et al.

FOREIGN PATENT DOCUMENTS

| EP | 2700632 A1 | 2/2014 |
|---|---|---|
| EP | 3618830 A1 | 3/2020 |
| WO | 2018203262 A1 | 11/2018 |
| WO | 2020222231 A1 | 11/2020 |

OTHER PUBLICATIONS

Janovak et al., European Journal of Pharmaceutical Sciences (2018), 123, pp. 79-88.*

Gao et al., ACS Appl. Mater. Interfaces (2018), 10, pp. 25228-25240.*

Ribas A, Wolchok JD. Cancer immunotherapy using checkpoint blockade. Science. 2018;359:1350-5. doi:10.1126/ science.aar4060.

Benci JL, Xu B, Qiu Y, Wu TJ, Dada H, Twyman-Saint Victor C, et al. Tumor Interferon Signaling Regulates a Multigenic Resistance Program to Immune Checkpoint Blockade. Cell. 2016; 167:1540-1554.e12. http://dx.doi.org/10.1016/j.cell.2016.11.022.

Pitt JM, Vétizou M, Daillère R, Roberti MP, Yamazaki T, Routy B, et al. Resistance Mechanisms to Immune-Checkpoint Blockade in Cancer: Tumor-Intrinsic and -Extrinsic Factors. Immunity. 2016;44:1255-69. http://dx.doi.org/10.1016/j.immuni.2016.06.001.

Syn NL, Teng MWL, Mok TSK, Soo RA. De-novo and acquired resistance to immune checkpoint targeting. The Lancet Oncology. 2017; 18:e731-41. doi: 10.1016/S1470-2045(17)30607-1. PMID: 29208439.

Segovia M, Russo S, Girotti MR, Rabinovich GA, Hill M. Role of inflammasome activation in tumor immunity triggered by immune checkpoint blockers. Clin Exp Immunol. 2020;200:155-62. doi: 10.1111/cei.13433.

Hill M, Segovia M, Russo S, Girotti M, Rabinovich GA. The Paradoxical Roles of Inflammation during PD-1 Blockade in Cancer. Trends Immunol. 2020;41:982-93. https://doi.org/10.1016/j.it. 2020.09.003.

Freeman TL, Swartz TH. Targeting the NLRP3 Inflammasome in Severe COVID-19. Front Immunol. 2020; 11:1518. doi: 10.3389/ fimmu.2020.01518.

(Continued)

*Primary Examiner* — Brian J Davis
(74) *Attorney, Agent, or Firm* — The Roy Gross Law Firm, LLC; Roy D. Gross

(57) ABSTRACT

This invention is related to an anti-tumoral composition for the treatment of neoplastic pathologies of malignant kind, and for the treatment of eg7 thymic lymphoma. Said composition comprises a TMEM176A/B inhibitor formulated in nanoparticles. This invention is also related to a method of treating neoplastic pathologies of malignant kind. Said method comprises the steps of administering to a subject a TMEM176A/B inhibitor formulated in nanoparticles.

3 Claims, 34 Drawing Sheets

(56)                    References Cited

OTHER PUBLICATIONS

Segovia M, Louvet C, Charnet P, Savina A, Tilly G, Gautreau L, et al. Autologous Dendritic Cells Prolong Allograft Survival Through Tmem176b -Dependent Antigen Cross-Presentation: Immunoregulatory Mechanisms of Autologous DCs. American Journal of Transplantation. 2014;14:1021-31. doi: 10.1111/ajt.12708.

Eon Kuek L, Leffler M, Mackay GA, Hulett MD. The MS4A family: counting past 1, 2 and 3. Immunol Cell Biol. 2016;94:11-23. doi:10.1038/icb.2015.48.

Louvet C, Chiffoleau E, Heslan M, Tesson L, Heslan J-M, Brion R, et al. Identification of a New Member of the CD20/FcepsilonRIbeta Family Overexpressed in Tolerated Allografts. American Journal of Transplantation. 2005;5:2143-53. doi: 10.1111/j.1600-6143.2005. 01007.x.

Condamine T, Le Texier L, Howie D, Lavault A, Hill M, Halary F, et al. Tmem176B and Tmem176A are associated with the immature state of dendritic cells. J Leukoc Biol. 2010;88:507-15. DOI: 10.1189/jlb.1109738.

Villani A-C, Satija R, Reynolds G, Sarkizova S, Shekhar K, Fletcher J, et al. Single-cell RNA-seq reveals new types of human blood dendritic cells, monocytes, and progenitors. Science. 2017;356:eaah4573. doi:10.1126/science.aah4573.

Bourdely P, Anselmi G, Vaivode K, Ramos RN, Missolo-Koussou Y, Hidalgo S, et al. Transcriptional and Functional Analysis of CD1c+ Human Dendritic Cells Identifies a CD163+ Subset Priming CD8+CD103+ T Cells. Immunity. 2020;53:335-352.e8. https://doi.org/10.1016/j.immuni.2020.06.002.

Brown CC, Gudjonson H, Pritykin Y, Deep D, Lavallée V-P, Mendoza A, et al. Transcriptional Basis of Mouse and Human Dendritic Cell Heterogeneity. Cell. 2019; 179:846-863.e24. https://doi.org/10.1016/j.cell.2019.09.035.

Segovia M, Russo S, Jeldres M, Mahmoud YD, Perez V, Duhalde M, et al. Targeting TMEM176B Enhances Antitumor Immunity and Augments the Efficacy of Immune Checkpoint Blockers by Unleashing Inflammasome Activation. Cancer Cell. 2019;35:767-781.e6. https://doi.org/10.1016/j.ccell.2019.04.003.

Rathinam VAK, Fitzgerald KA. Inflammasome Complexes: Emerging Mechanisms and Effector Functions. Cell. 2016;165:792-800. http://dx.doi.org/10.1016/j.cell.2016.03.046.

Liu Z, An H, Song P, Wang D, Li S, Chen K, et al. Potential targets of TMEM176A in the growth of glioblastoma cells. OTT. 2018; vol. 11:7763-75. DOI: 10.2147/OTT.S179725.

Sun L, Zhang Y, Zhang C. Distinct expression and prognostic value of MS4A in gastric cancer. Open Medicine. 2018;13:178-88. https://doi.org/10.1515/med-2018-0028.

Theisen DJ, Davidson JT, Briseño CG, Gargaro M, Lauron EJ, Wang Q, et al. WDFY4 is required for cross-presentation in response to viral and tumor antigens. Science. 2018;362:694-9. doi:10.1126/science.aat5030.

Alloatti A, Rookhuizen DC, Joannas L, Carpier J-M, Iborra S, Magalhaes JG, et al. Critical role for Sec22b-dependent antigen cross-presentation in antitumor immunity. J Exp Med. 2017;214:2231-41. https://doi.org/10.1084/jem.20170229.

Savina A, Jancic C, Hugues S, Guermonprez P, Vargas P, Moura IC, et al. NOX2 controls phagosomal pH to regulate antigen processing during crosspresentation by dendritic cells. Cell. 2006; 126:205-18. DOI 10.1016/j.cell.2006.05.035.

Jancic C, Savina A, Wasmeier C, Tolmachova T, El-Benna J, Dang PM-C, et al. Rab27a regulates phagosomal pH and NADPH oxidase recruitment to dendritic cell phagosomes. Nat Cell Biol. 2007;9:367-78. DOI: 10.1038/ncb1552.

Savina A, Amigorena S. Phagocytosis and antigen presentation in dendritic cells. Immunol Rev. 2007;219:143-56. DOI: 10.1111/j. 1600-065X.2007.00552.x.

Savina A, Peres A, Cebrian I, Carmo N, Moita C, Hacohen N, et al. The Small GTPase Rac2 Controls Phagosomal Alkalinization and Antigen Crosspresentation Selectively in CD8+ Dendritic Cells. Immunity. 2009;30:544-55. DOI 10.1016/j.immuni.2009.01.013.

Howland SW, Wittrup KD. Antigen Release Kinetics in the Phagosome Are Critical to Cross-Presentation Efficiency. The Journal of Immunology. 2008;180:1576-83. doi: 10.4049/jimmunol.180.3. 1576.

Lazaridou M, Christodoulou E, Nerantzaki M, Kostoglou M, Lambropoulou D, Katsarou A, et al. Formulation and In-Vitro Characterization of Chitosan-Nanoparticles Loaded with the Iron Chelator Deferoxamine Mesylate (DFO). Pharmaceutics. 2020;12:238. doi: 10.3390/pharmaceutics12030238. PMID: 32156022; PMCID: PMC7150847.

Cha J, Lee WB, Park CR, Cho YW, Ahn C-H, Kwon IC. Preparation and characterization of cisplatin-incorporated chitosan hydrogels, microparticles, and nanoparticles. Macromol Res. 2006; 14:573-8. https://doi.org/10.1007/BF03218726.

Torrecilla D, Lozano M V., Lallana E, Neissa JI, Novoa-Carballal R, Vidal A, et al. Anti-tumor efficacy of chitosan-g-poly (ethylene glycol) nanocapsules containing docetaxel: Anti-TMEFF-2 functionalized nanocapsules vs. non-functionalized nanocapsules. European Journal of Pharmaceutics and Biopharmaceutics. Elsevier B.V.; 2013;83:330-7. http://dx.doi.org/10.1016/j.ejpb.2012.10.017.

Hamilton, Susan L., et al. "A comparison between the binding and electrophysiological effects of dihydropyridines on cardiac membranes." Molecular pharmacology 31.3 (1987): 221-231. PMID: 2436031.

Segovia M, Cuturi MC, Hill M. Preparation of mouse bone marrow-derived dendritic cells with immunoregulatory properties. Methods in molecular biology (Clifton, NJ). United States; 2011;677:161-8.

Livak KJ, Schmittgen TD. Analysis of relative gene expression data using real-time quantitative PCR and the 2(-Delta Delta C(T)) Method. Methods (San Diego, Calif). United States; 2001;25:402-8. doi:10.1006/ meth.2001.1262.

Karttunen J, Sanderson S, Shastri N. Detection of rare antigen-presenting cells by the lacZ T-cell activation assay suggests an expression cloning strategy for T-cell antigens. Proceedings of the National Academy of Sciences. 1992;89:6020-4. doi: 10.1073/pnas. 89.13.6020. PMID: 1378619; PMCID: PMC402130.

Thomas, Gunter, Minn Chung, and Charles J. Cohen. "A dihydropyridine (Bay k 8644) that enhances calcium currents in guinea pig and calf myocardial cells. A new type of positive inotropic agent." Circulation research 56.1 (1985): 87-96 doi: 10.1161/01.res.56.1.87. PMID: 2578336.

Hoshyar N, Gray S, Han H, Bao G. The effect of nanoparticle size on in vivo pharmacokinetics and cellular interaction. Nanomedicine (London, England). 2016;11:673-92. doi: 10.2217/nnm.16.5. Epub Mar. 22, 2016. PMID: 27003448; PMCID: PMC5561790.

Fan W, Yan W, Xu Z, Ni H. Formation mechanism of monodisperse, low molecular weight chitosan nanoparticles by ionic gelation technique. Colloids and surfaces B, Biointerfaces. Netherlands; 2012;90:21-7. doi:10.1016/j.colsurfb.2011.09.042.

Mitchell MJ, Billingsley MM, Haley RM, Wechsler ME, Peppas NA, Langer R. Engineering precision nanoparticles for drug delivery. Nat Rev Drug Discov. 2021;20:101-24. https://doi.org/10.1038/s41573-020-0090-8.

Marques C, Som C, Schmutz M, Borges O, Borchard G. How the Lack of Chitosan Characterization Precludes Implementation of the Safe-by-Design Concept. Front Bioeng Biotechnol. 2020;8:165. doi: 10.3389/fbioe.2020.00165.

Demaria O, Cornen S, Daëron M, Morel Y, Medzhitov R, Vivier E. Harnessing innate immunity in cancer therapy. Nature. 2019;574:45-56. https://doi.org/10.1038/s41586-019-1593-5.

Rodell CB, Arlauckas SP, Cuccarese MF, Garris CS, Li R, Ahmed MS, et al. TLR7/8-agonist-loaded nanoparticles promote the polarization of tumour-associated macrophages to enhance cancer immunotherapy. Nat Biomed Eng. 2018;2:578-88. doi:10.1038/s41551-018-0236-8.

Luo M, Wang H, Wang Z, Cai H, Lu Z, Li Y, et al. A STING-activating nanovaccine for cancer immunotherapy. Nature Nanotech. 2017; 12:648-54. doi:10.1038/nnano.2017.52.

Shae D, Becker KW, Christov P, Yun DS, Lytton-Jean AKR, Sevimli S, et al. Endosomolytic polymersomes increase the activity of cyclic dinucleotide STING agonists to enhance cancer immunotherapy. Nat Nanotechnol. 2019; 14:269-78. doi:10.1038/s41565-018-0342-5.

(56) References Cited

OTHER PUBLICATIONS

Gong N, Zhang Y, Teng X, Wang Y, Huo S, Qing G, et al. Proton-driven transformable nanovaccine for cancer immunotherapy. Nat Nanotechnol. 2020;15:1053-64. doi:10.1038/s41565-020-00782-3.

Mohammed, Munawar A., et al. "An overview of chitosan nanoparticles and its application in non-parenteral drug delivery." Pharmaceutics 9.4 (2017): 53. doi:10.3390/pharmaceutics9040053.

PCT International Search Report for International Application No. PCT/IL2022/050587, mailed Sep. 15, 2022, 3pp.

PCT Written Opinion for International Application No. PCT/IL2022/050587, mailed Sep. 15, 2022, 6pp.

PCT International Preliminary Report on Patentability for International Application No. PCT/IL2022/050587, issued Nov. 21, 2023, 7pp.

Choochottiros, Chantiga & Yoksan, Rangrong & Chirachanchai, Suwabun. (2009). Amphiphilic chitosan nanospheres: Factors to control nanosphere formation and its consequent pH responsive performance. Polymer. 50. 1877-1886. 10.1016/j.polymer.2009.02.029.

European Patent Office, Extended European Search Report for European Patent Application No. 22815506.5, dated Apr. 22, 2025, 10pp.

* cited by examiner eNP                                    NP-BayK8644

MEANS AND METHODS FOR IMPROVING ANTI-TUMORAL EFFICACY OF TRANSMEMBRANE CHANNEL PROTEIN BLOCKERS

CROSS-REFERENCE TO RELATED APPLICATIONS

This application is a National Phase of PCT Patent Application No. PCT/IL2022/050587, having International filing date of Jun. 2, 2022, which claims priority from U.S. Provisional Patent Application No. 63/196,260, filed on Jun. 3, 2021, the disclosures of which are incorporated by reference in their entirety herein.

TECHNICAL FIELD OF THE INVENTION

The invention generally pertains to means and methods for improving anti-tumoral efficacy of transmembrane channel protein blockers. More specifically, the invention relates to formulating TMEM176B blocker/inhibitor BayK8644 in nanoparticles for improving its anti-tumoral efficacy by reinforcing CD8$^+$ T cells.

BACKGROUND OF THE INVENTION

Immunotherapeutic approaches have revolutionized cancer therapy (1). However, only a minority of treated patients have clinical benefits (2-4). Thus, there is a need to identify and target novel immunoregulatory molecules to trigger effective anti-tumoral immune responses.

In this context, TMEM176B, an intracellular acid-sensitive non-specific cation channel, has been proposed as an emergent player in immunoregulation (5-7).

High TMEM176A/B expression has been associated with diminished overall survival in patients with colon (15), glioblastoma (17) and gastric cancer (18). Those data therefore support TMEM176A/B as potential pharmacological targets in oncology. Indeed, pharmacological and genetic evidence has shown that targeting TMEM176B triggers strong anti-tumoral immune responses which depend on host inflammasome activation and CD8$^+$ T cell responses (15). However, In vivo TMEM176A/B blockade with BayK8644 controlled tumor growth in murine cancer models in preventive but not in therapeutic protocols (mice bearing established tumors) (15).

SUMMARY OF THE INVENTION

The present invention relates generally to the field of means and methods for improving anti-tumoral efficacy of transmembrane channel protein blockers and more specifically, to an anti-tumoral composition, for the treatment of neoplastic pathologies of malignant kind.

The object of the present invention to disclose the composition as defined in any of the above, wherein said composition comprises a TMEM176A/B inhibitor encapsulated in Chitosan nanoparticles.

It is another object of the present invention to disclose the composition as defined in any of the above, wherein said TMEM176A/B inhibitor is (+)BayK8644 encapsulated in Chitosan nanoparticles.

It is another object of the present invention to disclose the composition as defined in any of the above, wherein said encapsulated TMEM176A/B inhibitor is selected from a group consisting of aconitine, procainamide, lidocaine, and propaphenon and any combination thereof.

It is another object of the present invention to disclose the composition as defined in any of the above, wherein said composition of encapsulated TMEM176A/B inhibitor allows slow release of said TMEM176A/B inhibitor, thus preventing inhibition of antigen cross-presentation while strongly triggering inflammasome activation.

It is another object of the present invention to disclose the composition as defined in any of the above, wherein said composition is configured to be administrable in a manner selected from a group consisting of slow release, sustained release, controlled release and any combination thereof.

It is another object of the present invention to disclose the composition as defined in any of the above, wherein said composition comprises a TMEM176A/B inhibitor encapsulated in Chitosan nanoparticles.

It is another object of the present invention to disclose a method of treating neoplastic pathologies of malignant kind, wherein said method comprises the steps of administering to a subject a tmem176a/b inhibitor formulated in nanoparticles.

It is another object of the present invention to disclose the method as defined in any of the above, wherein said TMEM176A/B inhibitor is selected from a group consisting of aconitine, procainamide, lidocaine, and propaphenon and any combination thereof.

Unless otherwise defined herein, all technical and/or scientific terms used herein have the same meaning as commonly understood by one of ordinary skill in the art to which the invention pertains. Although methods and materials similar or equivalent to those described herein may be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE FIGURES

Exemplary non-limited embodiments of the disclosed subject matter will be described, with reference to the following description of the embodiments, in conjunction with the figures.

The figures are generally not shown to scale and any sizes are only meant to be exemplary and not necessarily limiting. Corresponding or like elements are optionally designated by the same numerals or letters.

DETAILED DESCRIPTION OF THE PREFERRED EMBODIMENTS

Figure 1A:
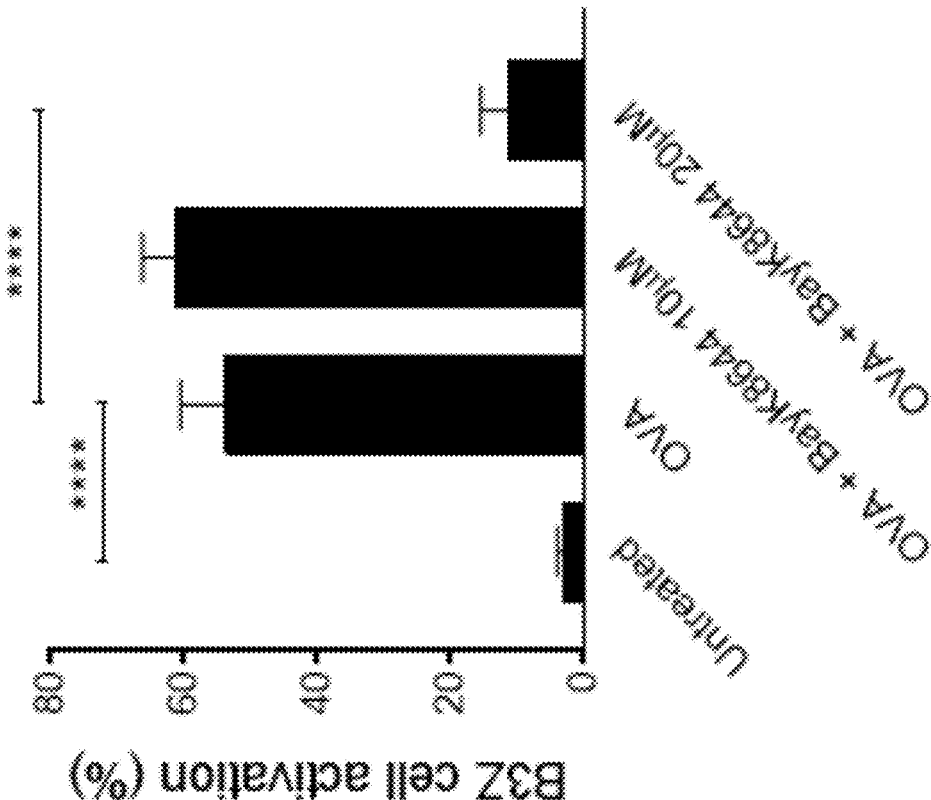
FIG. 1A-B. Free BayK8644 inhibits cross presentation in splenic dendritic cells.

The following description is provided, alongside all chapters of the present invention, so as to enable any person skilled in the art to make use of said invention and sets forth the best modes contemplated by the inventor of carrying out this invention. Various modifications, however, are adapted to remain apparent to those skilled in the art, since the generic principles of the present invention have been defined specifically to provide compositions and methods for improving anti-tumoral efficacy of transmembrane channel protein blockers. More specifically, the invention relates to formulating TMEM176B blocker, such as BayK8644, in nanoparticles for improving its anti-tumoral efficacy by reinforcing CD8+ T cells.

Throughout this specification, unless the context requires otherwise, the word "comprise" or variations such as "comprises" or "comprising", will be understood to imply the inclusion of a stated integer or group of integers but not the exclusion of any other integer or group of integers.

The terms TMEM176A and TMEM176B refer hereafter to transmembrane protein that in humans are encoded by the TMEM176A and TMEM176B genes, respectively. These are intracellular acid-sensitive non-specific cation channel which belong to the MS4A family (8-10). TMEM176B and TMEM176A are members of the CD20-like MS4A family. These are ubiquitous proteins highly expressed by macrophages and dendritic cells (DCs). TMEM176A and TMEM176B are strongly expressed by mouse, rat and human DCs (8, 10-14) among other leukocyte subsets. Functionally, TMEM176B plays a key role in tolerogenic DCs to prolong allograft survival (8). Moreover, we have shown that TMEM176B inhibits the NLRP3 inflammasome activation through ionic mechanisms in mouse and human DCs and macrophages (15). Inflammasomes are cytosolic multiprotein complexes that sense cellular stress and lead to Caspase-1-dependent activation of IL-1$\beta$ and IL-18 (16).

The term BayK8644 refers hereafter to a chiral dihydropyridine (DHP), a modulator of L-type calcium channels. Its two enantiomers have opposite effects on L-type voltage-gated Ca2+ channels. Specifically, (+)-BayK8644 is an inhibitor of L-type Ca++ channels. In contrast, (−)-BayK8644 and the racemic mixture are agonists of those channels (45).

As recently shown (15), in vivo TMEM176A/B blockade with (+)-BayK8644 controlled tumor growth in a Tmem176b, Casp1/11 and CD8-dependent manner in murine cancer models in preventive but not in therapeutic protocols (mice bearing established tumors).

Our speculation is that pharmacological blockade of TMEM176B may impair antigen cross-presentation, a critical pathway to trigger anti-tumoral CD8$^+$ T cell responses (19,20), and thus limit the therapeutic efficacy of (+)-BayK8644. Indeed, Tmem176b$^{-/-}$ DCs showed undermined capacities of cross-presenting antigens to CD8$^+$ T cells (8). Limited V-ATPase-dependent phagosomal acidification and transient alkalinized phagosomal pH were observed in Tmem176b$^{-/-}$ DCs during the first 30 minutes after phagocytosis, potentially explaining the cross-presentation defect (8). In fact, phagosomal pH is kept near neutrality by DCs to allow antigens to be cross-presented (21-24). Moreover, endo-phagosomal antigen processing occurs through a fast kinetic, since a time limit of 25 minutes has been proposed (25). Thus, exogenous antigens that were not processed before that time, would not be presented on MHC class I molecules (25). We therefore speculated that formulating (+)-BayK8644 through a strategy that allows a slow release kinetic in endosomes may prevent inhibition of cross-presentation by the compound while potentially maintaining its capacity to induce inflammasome activation.

The term Chitosan refers hereafter to the most important derivative of chitin, produced by removing the acetate moiety from chitin. It is derived from crustacean shells such as those from prawns or crabs, as well as from the cell walls of fungi. It is a naturally occurring polysaccharide, cationic, highly basic, mucoadhesive biocompatible polymer and approved by the U.S. FDA for tissue engineering and drug delivery (43)

Chitosan nanoparticles (NPs) are known to slowly release hydrophobic compounds within hours in a process that is accelerated by acidic pH (26, 27). Thus, chitosan NPs should avoid (+)-BayK8644 release in compartments such as early endosomes with neutral pH where antigen processing for cross-presentation is thought to take place. Once cross-presentation occurred, (+)-BayK8644 release might still trigger inflammasome activation.

The current invention demonstrates that BayK8644 does inhibit antigen cross-presentation. (+)-BayK8644 encapsulation in NPs (NP-PEG-BayK8644) prevents such inhibition while still triggering inflammasome activation. NP-PEG-BayK8644 controlled tumor growth of established tumors in a Tmem176b-dependent manner. Tumor control was associated with increased inflammasome activation by DCs the in tumor-draining lymph nodes (TDLN) and with tumor infiltration by total and tumor-specific CD8$^+$ T cells within the NP-PEG-BayK8644-treated animals. Thus, formulating (+)-BayK8644 in NPs improved the anti-tumoral efficacy of the compound by triggering inflammasome activation while preventing the inhibition of antigen cross-presentation.

Example 1

Materials and Methods:

Nanoparticle Synthesis—Synthesis of CS-PEG copolymer: 100 mg of chitosan-HCl (Protasan UP CL113), 27.6 mg of MeO-PEG-COOH, 2.4 mg Biotin-PEG-CO$_2$H and 3.4 mg of NHS were dissolved in 14 mL of water. Then, 69 mg of EDC was added in four equal portions every 30 minutes. The resulting solution was stirred for 24 hr at room temperature, and then was ultrafiltered (Amicon 10 KDa) with water and lyophilized to give chitosan-PEG as a white foam.

Preparation of CS nanoparticles: Synthesis of blank chitosan nanoparticles (NpCS) were prepared by using the solvent displacement technique, described by Torrecilla et al. ((28)) based on the solvent displacement method, with some modifications. Briefly, 40 mg of Lecithin were dissolved in 0.5 mL of ethanol before adding 125 µL of Crodamol and 9.5 mL of acetone. This organic phase was directly poured over 20 mL of aqueous phase containing 10 mg of CS and 50 mg of Poloxamer 188. The mixture turned milky immediately as a result of the formation of CSNp. Finally, solvents were evaporated under vacuum to a final volume of 10 mL. (+)-BayK8644 and fluorescent probe (6 coumarin) loaded CSNp formulations were prepared as described above by adding 0.5 mL of ethanolic (+)-BayK8644 solution (20 mg/mL) and 1 mL of ethanolic Coumarin solution (1 mg/mL) to the organic phase respectively. The final (+)-BayK8644 concentration obtained in CSNp was 1 mg/mL.

Nanoparticles' characterization—Particle size and zeta potential: Hydrodynamic diameter and zeta potential of samples were obtained using a Nano-ZetaSizer (Malvern Instruments Ltd., UK). Analyses were performed in aqueous medium at 25° C., viscosity of 0.8872 cP and RI of 1.33. Particle size was read in terms of z-average and zeta potential was calculated from measured electrophoretic mobility using the Helmoltz-Smoluchowski equation. Samples were analyzed in triplicate.

Surface Morphology

The morphology of the nanocarriers was examined by transmission electron microscopy (TEM), JEOL JEM-1010. Samples were stained with 2% (w/v) phosphotungstic acid solution and placed on copper grids (200-mesh) for viewing by TEM.

Encapsulation Efficiency of (+)-BayK8644-Loaded CSNp: The encapsulation efficiency of (+)-BayK8644 in the CSNp was determined indirectly by the difference between the total amount of (+)-BayK8644 in the formulation and the free drug found in the supernatant of the formulation. Consequently, the total amount of drug was estimated by dissolving an aliquot of nonisolated (+)-BayK8644-loaded CSNp with acetonitrile and measured with a high performance liquid chromatography (HPLC) system. The no encapsulated drug was determined by the same method following separation of the CS structures from the aqueous medium by ultracentrifugation. The HPLC system consisted of a Thermo Scientific Ultimate 3000 equipped with a UV detector set at 410 nm and a reverse phase Zorbax Extend 300 C18 column (4.6×150 mm i.d., pore size 3.5 m Agilent, U.S.A.). The mobile phase consisted of a mixture of acetonitrile:water (50:50 v/v). The standard calibration curves of (+)-BayK8644 were linear (r2>0.999) in the range of concentrations between 0.1-1.4 μg/mL.

Animals: Six-to-ten weeks old male or female C57BL/6 Tmem176b$^{+/+}$ (WT) and Tmem176b$^{-/-}$ mice were used (Jackson Lab; Bar Harbor, ME) and bred for up to 20 generations in the Transgenic and Experimental Animals Unit (UATE) of the Pasteur Institute in Montevideo in conditions free of specific pathogens (SPF). These were kept in a controlled environment, with a temperature between 19 and 21° C., and cycles of 14 hours of light and 10 hours of darkness. Mice received water and sterile ration administered under ad libitum conditions. Tmem176b$^{-/-}$ mice were generated in the 129/SvJ strain and heterozygous mice were backcrossed for 10 generations onto the C57BL/6 background (Janvier, Saint Berthevin, France) as reported in ((29)). All experiments were performed according to local regulation and approved by the Institutional Animal Care and Use Committee from Institut Pasteur de Montevideo.

Cell line culture: The E.G7-OVA (expressing OVA antigen) cell line (ATCC® CRL-2113™, (Manassas, VA), thymic lymphoma of murine origin) was cultured in DMEM medium supplemented with 10% fetal bovine serum (SBF), 10 mM HEPES, 1 mM sodium pyruvate, MEM-1% non-essential amino acids, 0.05 mM β-mercaptoethanol, penicillin/streptomycin 100 units/mL and 0.4 mg/mL geneticin. It was kept at 37° C. in the presence of 5% $CO_2$.

Tumor Models and Treatments: WT and Tmem176b$^{-/-}$ C57BL/6 mice were injected s.c with 0.5×10$^6$ E.G7-OVA thymic lymphoma cells. At the indicated experiment, injection was performed alternating one Tmem176b and one Tmem176b$^{-/-}$ mouse until completing both groups. In treated animals, alternation was done between (+)-BayK8644- and vehicle-treated animals or NP-BayK8644 and eNP-treated animals. Tumor growth was caliper measured manually every 2-3 days, and the two major diameters were taken. 70 nmoles of free (+)-BayK8644 or (+)-BayK8644 encapsulated in chitosan nanoparticles, or the same amount of empty NPs injections were repeated at the +2, +4, +6, +8 days after the first injection. Mice were sacrificed when one of the major tumor diameters reached 2 cm.

Primary culture of dendritic cells derived from bone marrow (BMDCs): Dendritic cells derived from bone marrow (BMDCs) were obtained performing the protocol described by Segovia et al ((30)). For this, the femurs and tibiae bone marrow was extracted of WT and Tmem176b$^{-/-}$ C57BL/6 mice. After red blood cells lysis, 5.0×10$^6$ cells were seeded in Petri dishes, in RPMI supplemented medium (10% fetal bovine serum, 10 mM HEPES, 1 mM sodium pyruvate, 1% non-essential MEM-amino acids, 2 mM L-glutamine, 0.05 mM β-mercaptoethanol, penicillin/streptomycin 100 units/mL). Thus, bone marrow-derived DCs were differentiated by culturing bone marrow cells for 8 days in the presence of 0.4 ng/mL GM-CSF. On day 3 and 6, the growth medium was renewed, adding GM-CSF to the culture each time. At day 8, adherent cells were >95% CD11c$^+$ CD11b$^+$MHC II$^{int}$ evaluated by flow cytometry analysis.

Nanoparticles uptake by Bone Marrow Dentritic Cells (BMDCs): At day 8, BMDCs were detached with a buffer solution containing SFB and EDTA. For confocal microscopy internalization studies, 1.0×10$^5$ cells were seeded in a 12-well plate, glass cover slips were previously placed in each well. Cells were allowed to adhere for 1.5 hours and stimulated for 30 minutes with 6 coumarin-NP at 37° C. to allow endocytosis process or 0° C. (as a negative control), washed and then chased for 15 minutes at the same conditions. All images were taken using a Zeiss LSM 800™ semi-spectral confocal laser scanning microscope (Beckman Coulter). For flow cytometry internalization studies, the same protocol was followed as mentioned above. BMDCS were collected and samples were acquired using Cyan ADP Flow Cytometer equipped with a 488 nm laser and a band filter (530/40 nm). For data analysis FlowJo v.X software (BD, Ashland, OR, USA) was used.

Colocalization Studies by Confocal Microscopy: Tmem176b$^{+/+}$ (WT) and Tmem176b$^{-/-}$ C57BL/6 BMDCs were plated in 12-well plate (1×10$^5$ cells/well) containing glass cover slips and cultured for 1.5 hours. Then cell were treated with 6-coumarin NPs during 30 minutes, washed and chased for 15 minutes. Cells were fixed in 2% (w/v) paraformaldehyde (PFA) for 15 min, permeabilized and blocked using TritonX100 0.1%, 3% BSA in PBS. Primary antibody, rabbit anti-mTMEM176B Polyclonal antibody (Proteintech Group) 5 μg/mL, or a control IgG antibody, was diluted in BSA-PBS-Triton solution and incubated overnight at 4° C. Three washing steps were performed using PBS solution. Biotina-donkey anti-Rabbit IgG (H+L) secondary antibody diluted 1:500 in BSA-PBS-Triton was added and incubated for 1.5 hours. After washing, cells were incubated with Streptavidin Alexa Fluor 568 conjugate (Molecular Probes) diluted 1:1000 in BSA-PBS-Triton. Finally, nuclei were stained with DAPI diluted 1:5000 (Life Technologies) and incubated for 5 minutes. Sections were mounted in ProLong antifade mounting medium (Molecular Probes). Fluorescence was observed by confocal microscopy Zeiss LSM 800™ semi-spectral.

In Vitro Inflammasome Activation: IL-1β was quantified in BMDCs culture supernatant as a readout of the NLRP3 inflammasome activation. As mentioned above, at day 8, 5.0×10$^4$ BMDCs were seeded in a 96-well plate, and allowed to adhere for 1.5 hours. Then, cells were stimulated for 3 hs with 0.25 μg/mL LPS, washed and treated for 2 hours with the indicated doses of free (+)-BayK8644, NP-BayK8644 and eNP. The presence of IL-1β was determined with a ELISA kit, according to the manufacturer protocol (Biolegend, 432603).

Caspase-1 activation was quantified in Tmem176b BMDCs culture as a readout of the NLRP3 inflammasome activation. As mentioned above, at day 8, BMDCs were seeded ($5\times10^5$ cells) in 35 mm culture dishes, and allowed to adhere for 1.5 hours. Cells were stimulated for 2 hr with 100 µM of free (+)-BayK8644, NP-BayK8644 and eNP and then washed. BMDCs were stained with FLICA-1 (FLICA 660 Caspase-1 Assay, ImmunoChemistry) for 30 minutes, and analyzed by flow cytometry using Cyan ADP Flow Cytometer equipped with a 488 nm laser and a band filter (530/40 nm). For data analysis FlowJo v.X software (BD, Ashland, OR, USA) was used.

Antigen cross-presentation assays in mouse splenic dendritic cells: To obtain splenic DCs, spleen of C57BL/6 mice was extracted, cut into small pieces and treated with collagenase-D (Roche, Merck). After 30 minutes of incubation at 37° C., the enzymatic reaction was stopped with a 10 mM EDTA solution. Lysis of red blood cells was performed with an ammonium chloride solution. Finally, cells were washed with PBS/SFB1%. For the isolation of CD11c$^+$ cells, murine anti-CD11c monoclonal antibodies coupled to magnetic microspheres supplied in the commercial kit "CD11c Micro-Beads UltraPure, mouse" (Miltenyi Biotec Inc, Auburn, CA, USA) were used according to the protocol suggested by the manufacturer. Briefly, splenic cells were labeled with anti-CD11c antibodies conjugated to the beads. The cells were allowed to pass through a magnetic column subjected to a magnetic field. Thereby, CD11c$^+$ cells were retained on the column. Then, the column was removed from the influence of the magnetic field and cells were eluted. The purity of the CD11c$^+$ fraction was confirmed by flow cytometry.

CD11c$^+$ spleen cells were incubated with 3 mg/mL of soluble OVA, or OVA plus 20 µM of free (+)-BayK8644, 20 µM of (+)-BayK8644 encapsulated into chitosan nanoparticles (NP-BayK8644) or empty counterpart (eNP) for 4 hours in supplemented-RPMI medium. Also, as a control, CD11c$^+$ spleen cells were incubated with SIINFEKL peptide at indicated concentrations or SIINFEKL peptide plus (+)-BayK8644 for 4 hours in supplemented-RPMI medium. Cells were then washed with PBS/BSA 1% and fixed with 0.008% glutaraldehyde for 3 minutes on ice and quenched with 0.2 M glycine solution. After one final wash with PBS, CD11c$^+$ spleen cells were incubated with the B3Z cell line (T cell hybridoma cell line) for 18 hours at 37° C. and 5% $CO_2$. B3Z cell line specific for SIINFEKL allowed us to study the T cells activation, and was kindly provided by Ignacio Cebrián (Membrane Fusion Laboratory, IHEM-CONICET; Faculty of Medical Sciences, UNCuyo). The B3Z cell line is a β-galactosidase (lacZ) inducible T cell hybridoma. They are stably transfected with the Dectin-1-CD3ζ (chimeric construct (Dectin-1 extracellular region fused to the CD3ζ (cytoplasmic region). Furthermore, these cells are transiently transfected with an NFAT-LacZ reporter gene (activated T-cell nuclear factor NFAT, fused to the *E. coli* lacZ gene); since CD3ζ (triggers an intracellular signal that leads to the activation of the transcriptional factor NFAT. Previous studies demonstrated that the heterologous lacZ gene, under the control of the complete enhancer region of IL-2 or NFAT alone, is specifically induced in transfected and activated T cells. Therefore, activation of transfected T cells results in the synthesis of the products of the IL-2 and lacZ genes. The activation of B3Z cell line was measured detecting β-galactosidase activity by optical density (absorbance at 595-655 nm) using chlorophenol red-β-D-galacto-pyranoside (CPRG; Roche) as substrate for the reaction.

Ex vivo isolation and flow cytometry analysis of CD8+ T cells: WT C57BL/6 mice were injected s.c with $0.5\times10^6$ EG7 thymic lymphoma cells. When tumors were palpable (tumor size of 5 mm×5 mm), 70 nmoles of (+)-BayK8644 encapsulated in NPs was intratumorally injected. NPs injections were repeated at the +2, +4 days after the first injection. After the third NP-BayK8644 injection, tumors were resected.

Animals treated with NP-BayK8644 were classified according to tumor growth kinetics. Those animals that control tumor growth over time (tumor size at the resection time were <100 mm$^2$) were named Responders. Inversely, those animals did not control the tumor size were called Progressors. T cells were isolated by dissociating tumor tissue in the presence of collagenase D (1 mg/ml) (Roche-Merck) for 10 min at 37° C. Reaction was stopped with EDTA 10 mM, and the suspension was filter through a 50 µm strainer. After red blood cell lysis, flow cytometry analysis was performed. For flow Cytometry analysis, single cell suspensions were stained with antibodies against surface molecules CD8α-APC-Cy7, TCRβ-PE, CD19-PercPCy5.5, OVA-pentamer-APC and TCRvβ12-FITC to discriminate EG.7-OVA tumor cells. All data were collected on a FACS Aria Fusion (BD Biosciences) and analyzed with FlowJo software (FlowJo v.X software (BD, Ashland, OR, USA).

Statistical analysis: Statistical analyses were performed by GraphPad Prism 7 (GraphPad Software, Inc., La Jolla, CA). Survival analyses were done with the Log-rank (Mantel-Cox) test. Comparison of two experimental conditions was done with unpaired Student's t test. Comparison of multiple conditions was done with one-way ANOVA tests. Differences in gene expression between responder and progressors groups were assessed using the unpaired t-test when normality assumption was met.

Figure 1B:
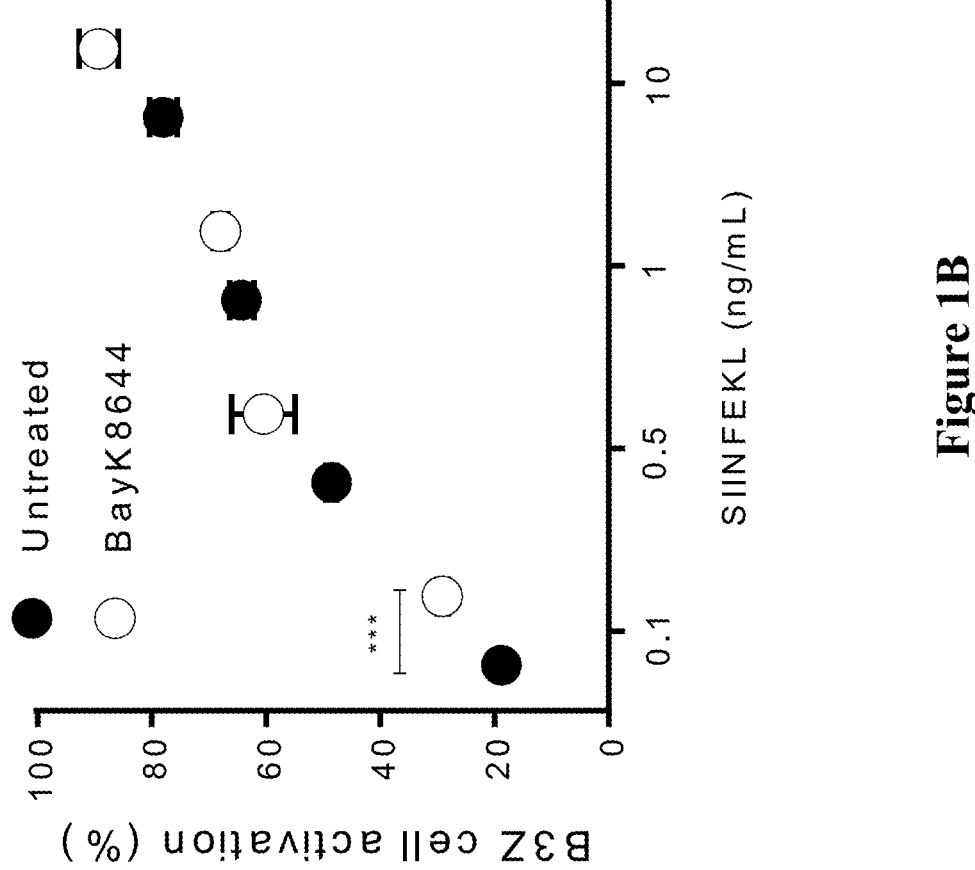

Results (+)-BayK8644 inhibits antigen cross-presentation by splenic DCs in vitro: We first studied whether (+)-BayK8644 inhibits antigen cross-presentation in vitro. Enriched splenic CD11c$^+$ DCs from WT mice were pulsed with OVA protein and co-cultured with the OVA-specific CD8$^+$ B3Z T cell hybridoma in which the 3-Gal enzyme is under the control of the IL-2 promoter (32). FIG. 1A-B depicts free (+)-BayK8644 in vitro inhibition of cross presentation in splenic dendritic cells: We observed that treating splenic DCs with (+)-BayK8644 significantly decreased their capacity to activate B3Z cells. CD11c$^+$ splenic DCs were loaded with 3 mg/ml soluble OVA for 4 hours ±10 µM or 20 µM of free (+)-BayK8644. Then, DCs were extensively washed, fixed, and cultured (18 hs) with the β-galactosidase-inducible B3Z T-cell hybrid, which is specific for the OVA peptide (SIINFEKL) in association with H-2Kb MIC-I molecules. B3Z T cell activation was measured by assessing β-galactosidase activity in a colorimetric assay. A pool of three independent experiments is shown. *p<0.001, p<0.0001. One-way ANOVA test. (FIG. 1A) Conversely, (+)-BayK8644 did not inhibit activation of B3Z cells induced by the minimal OVA peptide SIINFEKL Splenic DCs were loaded for 45 minutes with the OVA peptide SIINFEKL, which does not need further processing in intracellular compartments to be presented on H-2K$^b$ MHC-I molecules±20 µM (+)-BayK8644. DCs were then washed and fixed and co-cultured with B3Z T cells. A pool of three independent experiments are shown. *p<0.001, ****p<0.0001. Unpaired Student's t test. (FIG. 1B).

Thus, these results suggest that (+)-Bayk8644 interferes with the processing of OVA protein through the cross-presentation pathway in splenic DCs. Formulating (+)-BayK8644 through a strategy that avoids inhibition of cross-presentation may therefore improve the anti-tumoral immune responses triggered by the compound.

Encapsulation of (+)-BayK8644 in chitosan nanoparticles: Processing of antigens through the cross-presentation pathway is known to require fast kinetics (33). The rate of antigen release in endo-phagosomes directly affects cross-presentation efficiency, with an apparent time limit of 25 minutes post internalization for antigen release to be productive (33). Accordingly, transient alkalinized phagosomal pH during the first 30 minutes after phagocytosis was associated with impaired cross-presentation in Tmem176b$^{-/-}$ DCs (8). We therefore reasoned that formulating (+)-BayK8644 through a slow releasing mechanism in the endosomal compartment might avoid inhibition of cross-presentation by the compound. Chitosan nanoparticles (NPs) have been characterized as drug-encapsulating strategies that release compounds with a slow kinetic (26,27). We therefore speculated that encapsulating (+)-BayK8644 in chitosan NPs may avoid inhibition of cross-presentation by the compound while probably keeping its inflammasome-activation capacity.

Chitosan NPs (semi-crystalline linear polysaccharide composed of N-acetyl D-glucosamine and D-glucosamine units linked by β (1-4) glucosidic bonds) were synthesized and coated on their surface with polyethylene glycol (PEG), which forms a protective hydrophilic layer around the nanoparticles (28). Thus, empty pegylated NPs (eNP-PEG), pegylated NPs containing the compound (+)-BayK8644 (NP-PEG-BayK8644) and pegylated NPs containing the fluorescent probe 6-coumarin (NP-PEG-6cou) were synthesized. The average size, the polydispersity index (PI) and the Z potential of the NPs as well as the efficiency of encapsulation of the formulation containing (+)-BayK8644, are detailed in Table 1. The NPs size was obtained by using a Nano Zetasizer, showing an average size close to 200 nm, which is within the range of optimal sizes to improve the biological fluids circulation time of NPs, as well as for its cellular internalization (34). We can also conclude that the colloidal solutions obtained are stable, since their Z potential is less than 30 mV. The (+)-BayK8644 encapsulation efficiency in all the performed syntheses was always greater than 99%. FIG. 2 depicts Physicochemical characterization of chitosan nanoparticles (csNP).

Figure 2A:
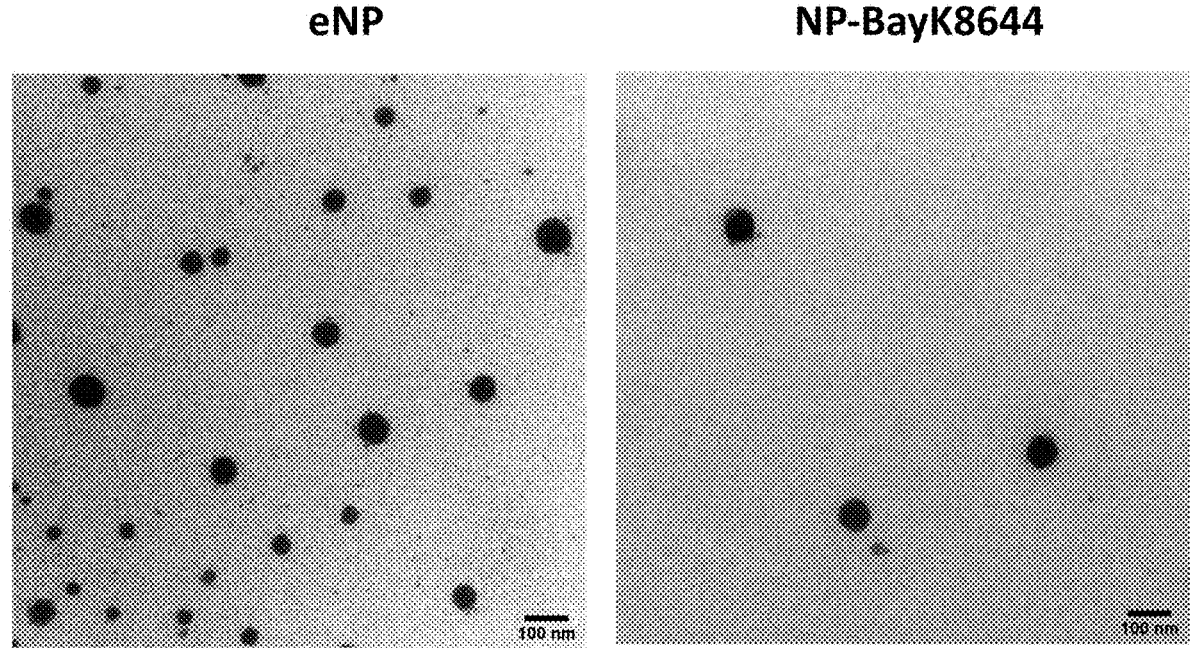
FIG. 2A-C. Physicochemical characterization of chitosan nanoparticles (csNP).

FIG. 2A depicts Transmission Electron Micrograph (TEM) images showing spherical morphology and physical diameter of csNPs. Note that csNPs sizes are fairly uniform and it reveals the conserved csNPs sizes distribution. In FIG. 2A, the TEM images of NP-BayK8644 and eNP show their spherical shape and a homogeneous size distribution. The sizes obtained by TEM are smaller than those obtained by Nano Zetasizer and are shown in Table 1. This difference in size measurement arises because in solution the ions of opposite charge will be attracted to the surface of the nanoparticles generating ionic layers that move along with it, and the Nano Zetasizer measures the nanoparticles hydrodynamic diameter in solution, while the TEM reports the actual diameter of the NPs without the ionic layer (35).

Figure 2B:
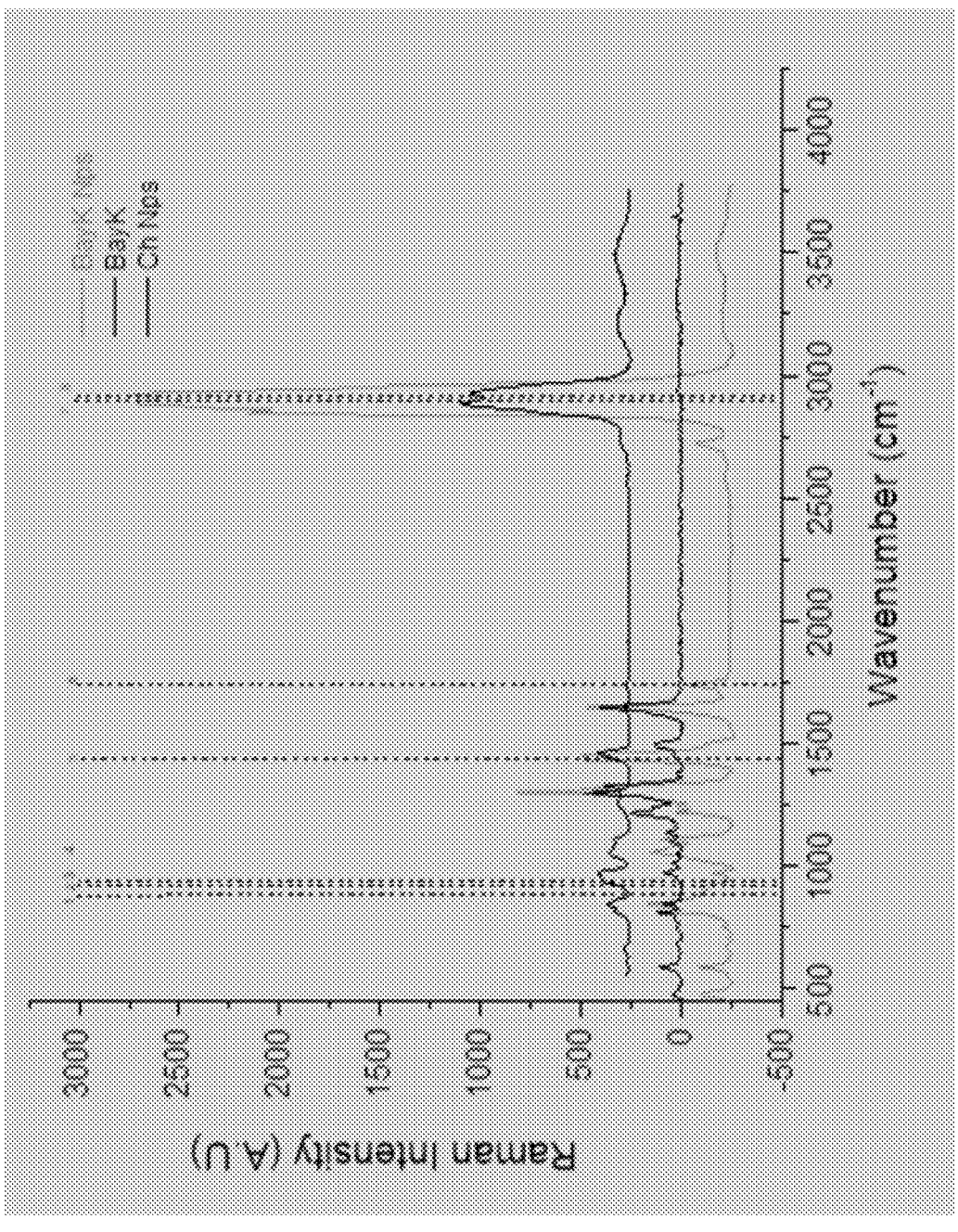

FIG. 2B, depicts the Raman spectrum of NP-BayK (in red), free (+)-BayK8644 (blue) and empty NP (black). This study by confocal Raman microscopy allowed to evaluate there are notorious differences between the spectra of pure (+)-BayK8644 and chitosan NPs with respect to that obtained with chitosan NPs loaded with (+)-BayK8644, obtaining a spectrum different from the one that would have been used. obtained only by adding the individual spectra. This indicates that there must have been a chemical interaction between the constituent materials of the NPs and the (+)-BayK8644 molecule. The latter is important when it comes to obtaining an adequate release of the (+)-BayK8644 molecule, which would occur from the lipid phase as the chitosan wall degrades.

Figure 2C:
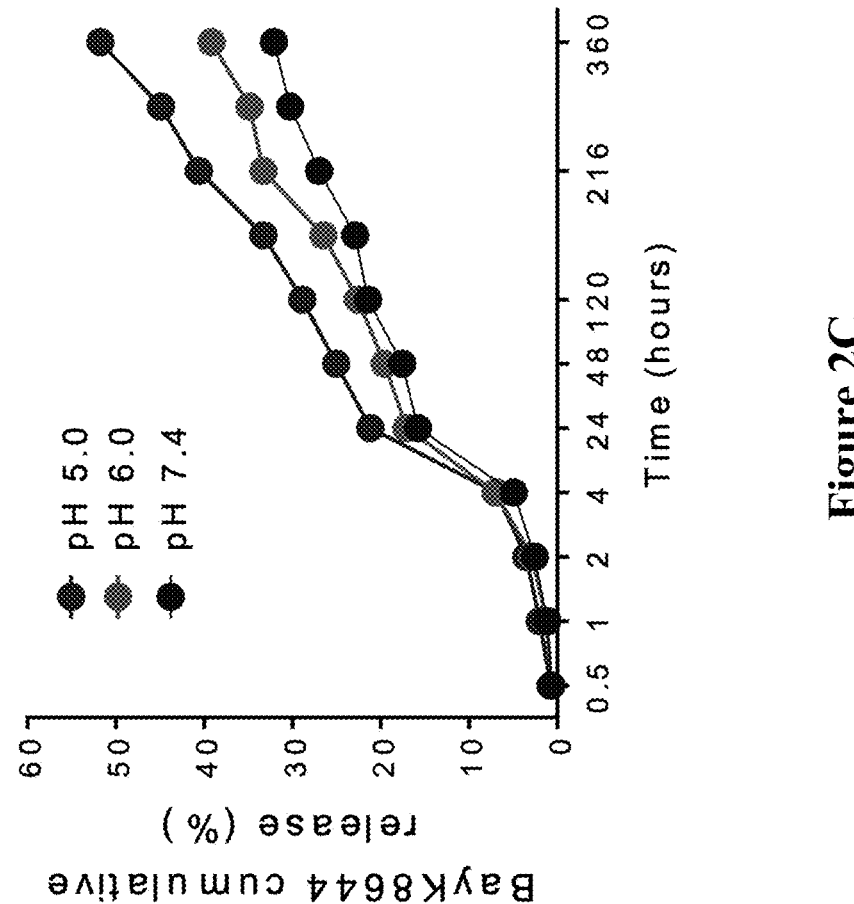

The in vitro release kinetics of (+)-BayK8644 from NPs at different pHs was also studied: FIG. 2C depicts cumulative drug release profiles of (+)-BayK8644-encapsulated NPs at different pH conditions. The NP-BayK8644 displayed a pH-dependent (+)-BayK8644 release profile. NP-BayK8644 solution was dissolved in RPMI culture media at the indicated pH (pH 5.0, pH 6.0 and pH 7.4). The amount of free (+)-BayK8644 released was determined by HPLC at different time points.

As expected (26,27), a slow kinetic release of the compound was observed. Acidic pH increased the percentage of released (+)-BayK8644 since 24 h incubation of the NPs with the buffer (FIG. 2C). Thus, encapsulation of (+)-BayK8644 in chitosan NPs is highly efficient, generates NPs with physicochemical characteristics compatible with their use with cells and releases the compound with a slow kinetic.

NP-PEG-BayK8644 do not inhibit antigen cross-presentation by DCs but still trigger inflammasome activation: To further determine whether encapsulation of (+)-BayK8644 in chitosan NPs may reinforce the anti-tumoral properties of the compound, we studied whether and how NPsBayK8644 modulate DCs biology. We therefore first assessed their internalization by DCs.

Figure 3A:
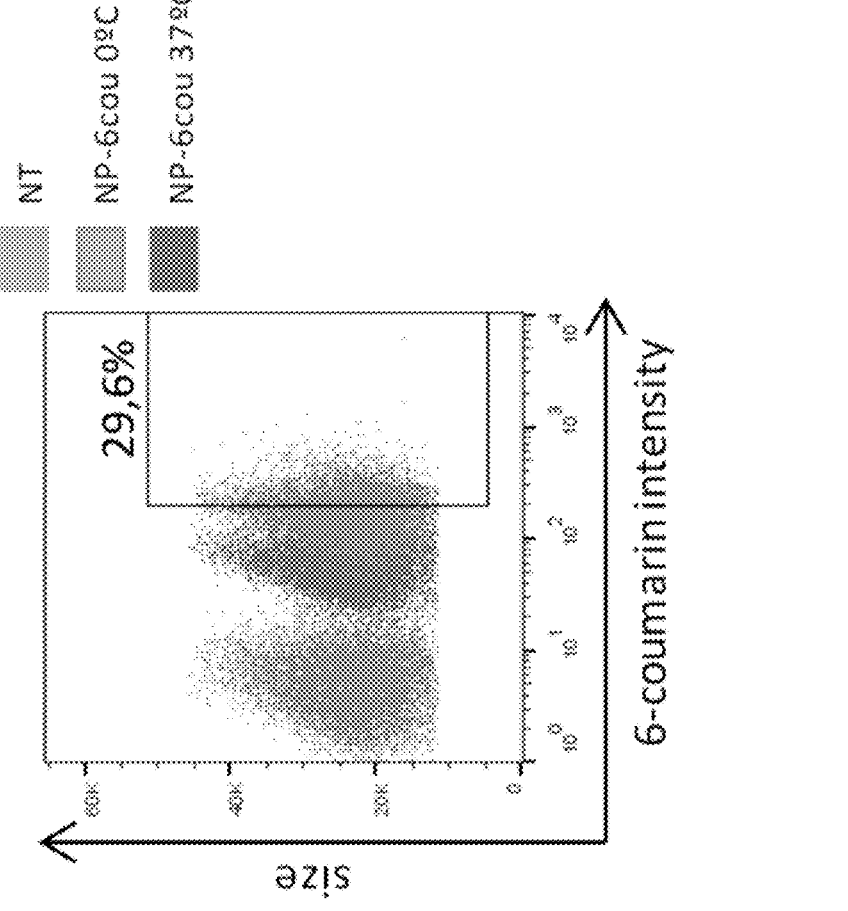
FIG. 3A-J. Chitosan nanoparticles are internalized by DCs, do not inhibit antigen cross-presentation and trigger inflammasome activation.

BMDCs were treated in vitro with 6-coumarin encapsulated NPs (NP-6cou) for 30 minutes, at 37° C. or 0° C. as a negative endocytosis control. A representative dot plot is shown with the percentage of 6-coumarin positive cells of BMDCs treated with NP-6cou at 37° C. (red dots), compared with BMDCs treated with 6-coumarinNP at 0° C. (cyan dots). Grey dots represent untreated BMDCs. (FIG. 3A)

Figure 3B:
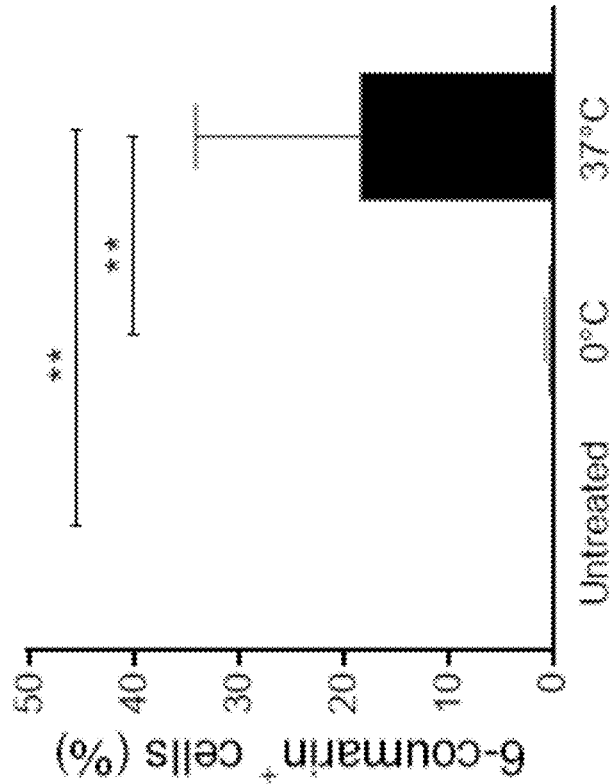
Figure 3C:
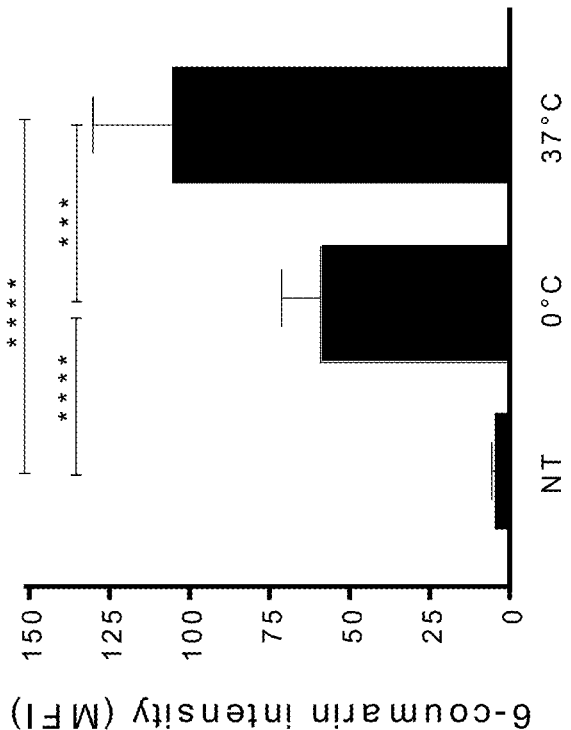

Specifically, FIG. 3B depicts percentage of 6-coumarin positive cells. A pool of three independent experiments is shown.  $p<0.01$, One-way ANOVA test., while FIG. 3C depicts Mean Fluorescence Intensity (MFI) of 6-coumarin dye determined by flow cytometry; * $p<0.001$; ****$p<0.0001$. One-way ANOVA test.

Flow cytometry studies showed that BMDCs efficiently internalizes NP-6cou, increasing both the percentage of 6cou$^+$ cells (FIG. 3A, 3B) and 6cou mean fluorescence

TABLE 1

| | | Physico-chemical properties of the nanosystems obtained (mean ± s.d.; n = 3) | | |
|---|---|---|---|---|
| Type of nanosystem | Size ± SD (nm) | PDI ± SD | Zeta potencial ± SD (mV) | Encapsulation efficiency (%) |
| csNP | 180.7 ± 15.0 | 0.249 ± 0.075 | 27.8 ± 1.3 | |
| csNP-PEG | 173.4 ± 4.1 | 0.218 ± 0.020 | 25.9 ± 5.7 | |
| csNP-PEG-BayK8644 | 209.9 ± 11.9 | 0.198 ± 0.032 | 24.6 ± 2.2 | 99.8 ± 0.1 |
| csNP-PEG-6cou | 199.1 ± 2.65 | 0.228 ± 0.006 | 24.2 ± 1.04 | | intensity (MFI) (FIG. 3A, 3C) in comparison to untreated cells and BMDCs incubated at 0° C. as a control to minimize active internalization.

Figure 3D:
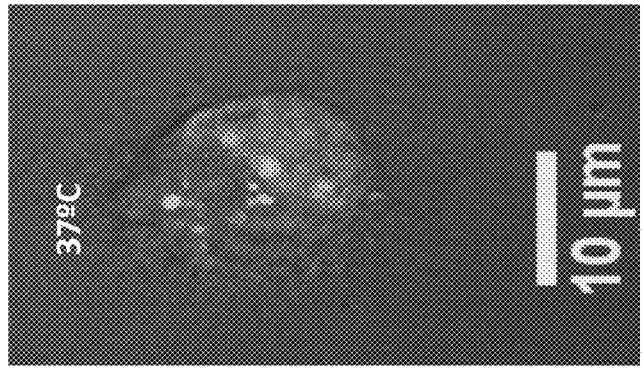
Figure 3D:
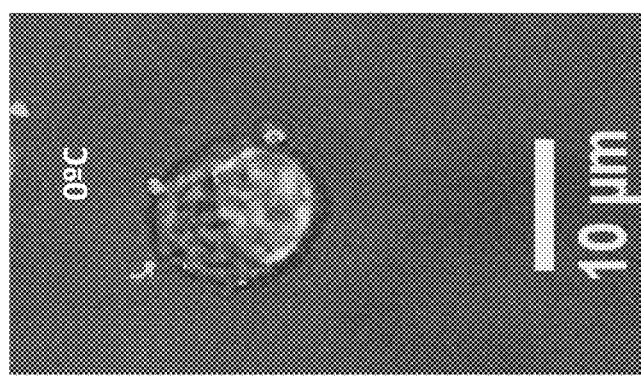
Figure 3D:
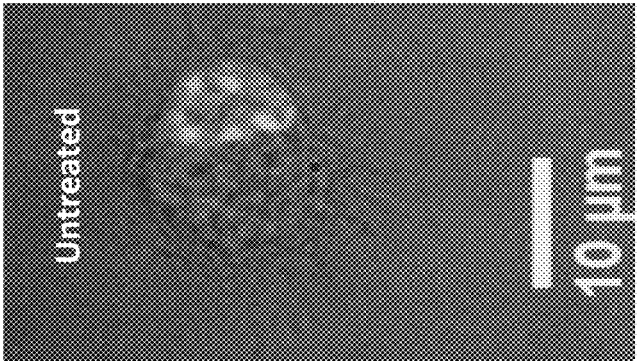

Confocal microscopy experiments showed that at 0° C. the NPs were lying at the cell surface, whereas at 37° C. the NPs were in fact within the BMDCs. FIG. 3D depicts Confocal microscopy analysis of BMDCs treated with NP-PEG-6cou (green fluorescence) at the indicated temperatures (0° C. and 37° C.). Nuclei were stained with DAPI (blue fluorescence). One experiment representative of three is shown. At least 50 cells were analyzed/experiment.

Moreover, we observed that NPs6-cou co-localized with the TMEM176B protein (FIG. 3E), suggesting that NPs are internalized by TMEM176B$^+$ endosomes (8). Thus, (+)-BayK8644 released by NPs within endosomes will be in proximity to TMEM176B.

Figure 3E:
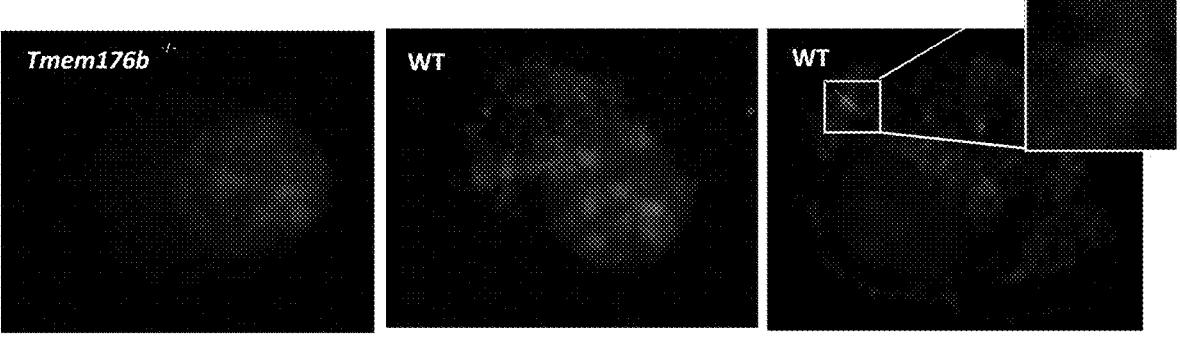
Figure 3E:
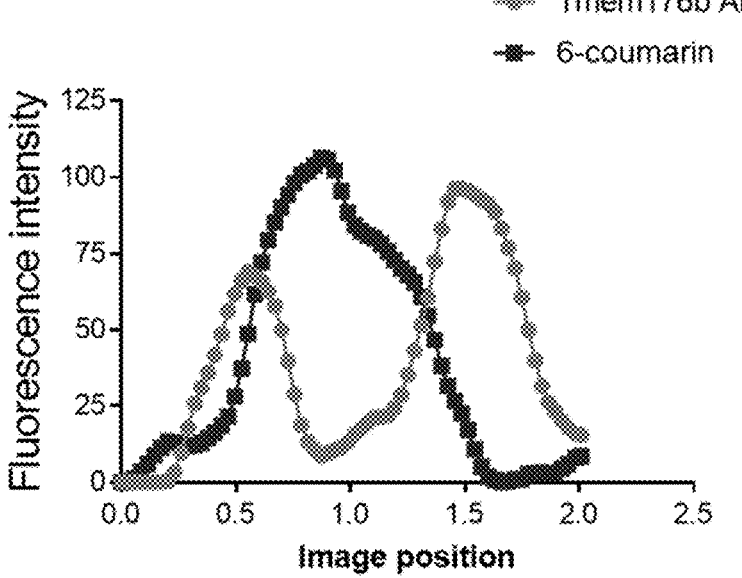

FIG. 3E depicts a Confocal microscopy study showing the colocalization of NP-PEG-6cou and the Tmem176b protein. BMDCs from Tmem176b (WT) mice and Tmem176b$^{-/-}$ mice were treated with NP-PEG-6cou for 30 minutes, then the immunostaining was performed with anti-Tmem176b (red) antibody. Nuclei were stained with DAPI (blue). The graph shows the colocalization representation by the intensity profiles of anti-TMEM176B staining (red) and NP-PEG-6cou (green) obtained using ImageJ software, along the indicated yellow line inside the white square. The fluorescence intensities are plotted along the y-axis and the image position along the x-axis. One experiment representative of three is shown. At least 50 cells were analyzed/experiment.

The study was further conducted to determine whether (+)-BayK8644 encapsulated in NPs may inhibit antigen cross-presentation by DCs. Splenic DCs were loaded with OVA protein±(+)-BayK8644 or ±NPBayK8644 and co-cultured with B3Z CD8$^+$ T cells. We observed that in contrast to (+)-BayK8644, NPBayK8644 failed to block activation of B3Z cells (FIG. 3F).

Figure 3F:
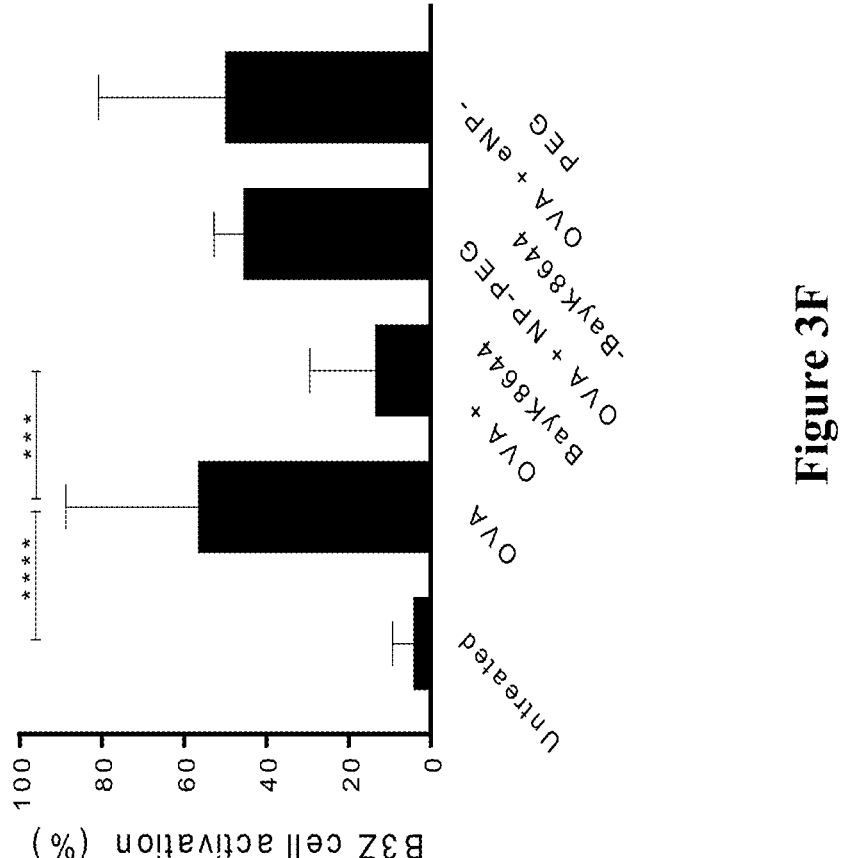

FIG. 3F shows that CD11c$^+$ splenic DCs were left untreated or loaded with 3 mg/ml soluble OVA for 4 hours±20 μM (+)-BayK8644, NP-PEG-BayK8644 or eNP-PEG. B3Z T cell activation was assessed through a colorimetric assay. A pool of three independent experiments is shown, *p<0.001, **p<0.0001. One-way ANOVA test.

Furthermore, treatment of DCs with NP-PEG-BayK8644 induced the secretion of IL-1β at higher levels than eNP-PEG in WT but not in Tmem176b$^{-/-}$ DCs.

Figure 3G:
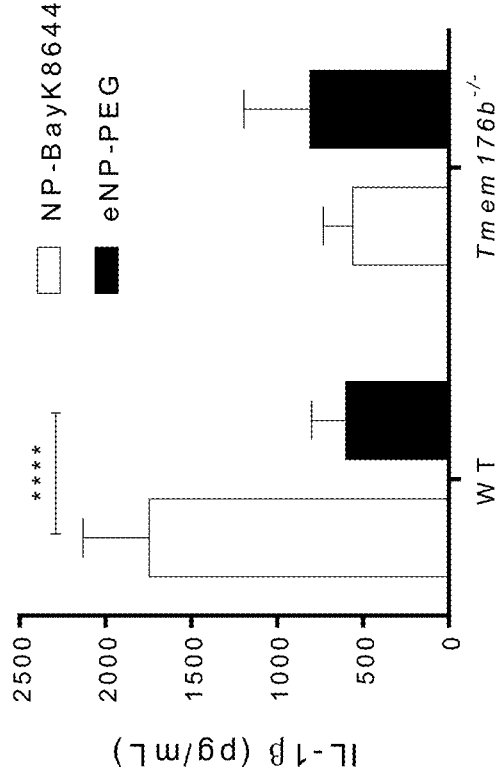

FIG. 3G depicts WT and Tmem176b$^{-/-}$ BMDCs were treated with LPS (0.25 μg/mL) for 3 hours, washed and exposed for 2 hours to 50 μM (+)-BayK8644 encapsulated in chitosan nanoparticles (NP-PEG-BayK8644), or an equivalent amount of empty NPs (eNP). IL-1β was measured in the culture supernatant by ELISA. One experiment representative of three is shown. ****p<0.0001. Two-way ANOVA test.

Figure 3H:
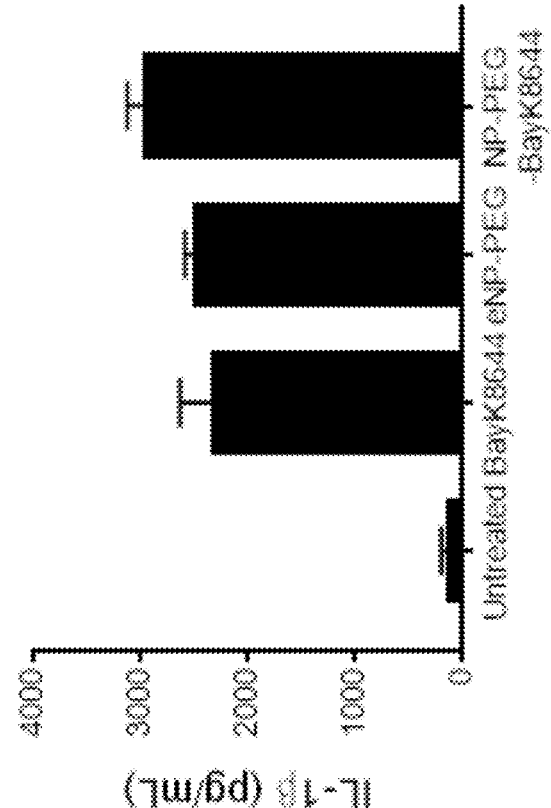

Moreover, NP-PEG-BayK8644 were at least as effective as (+)-BayK8644 in triggering IL-1β secretion. FIG. 3H, WT BMDCs were treated with LPS (0.25 μg/mL) for 3 hours, washed and exposed for 2 hours to 50 μM (+)-BayK8644 encapsulated in chitosan nanoparticles (NP-PEG-BayK8644), or an equivalent amount of empty NPs (eNP) or 50 μM free (+)-BayK8644. IL-1β was measured in the culture supernatant by ELISA. One experiment representative of three is shown.

Figure 3I:
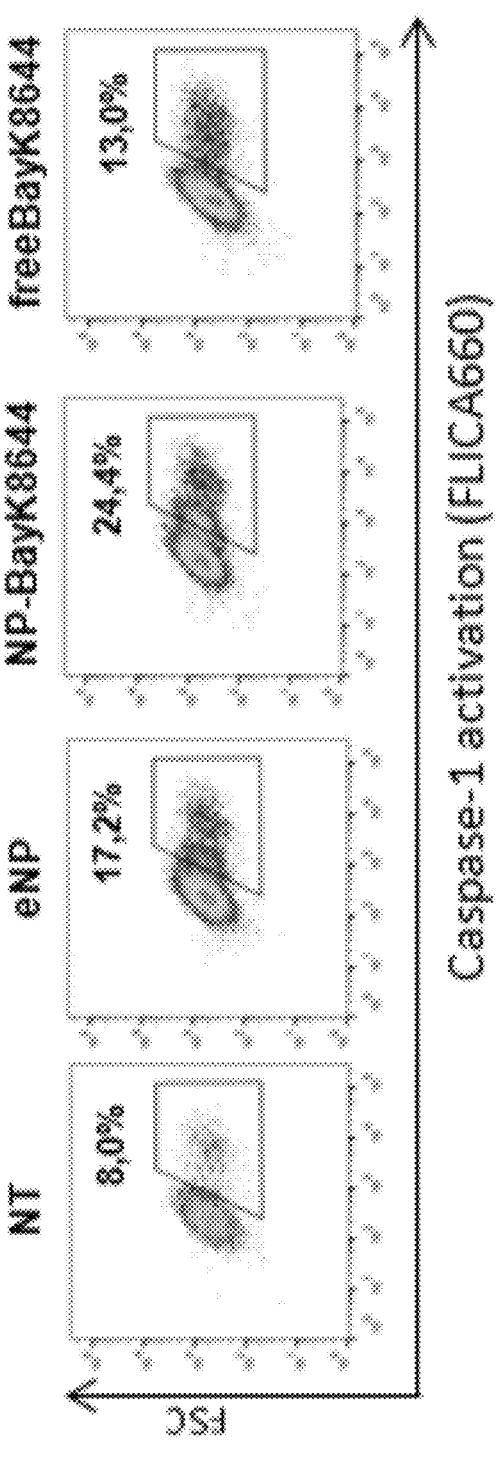
Figure 3J:
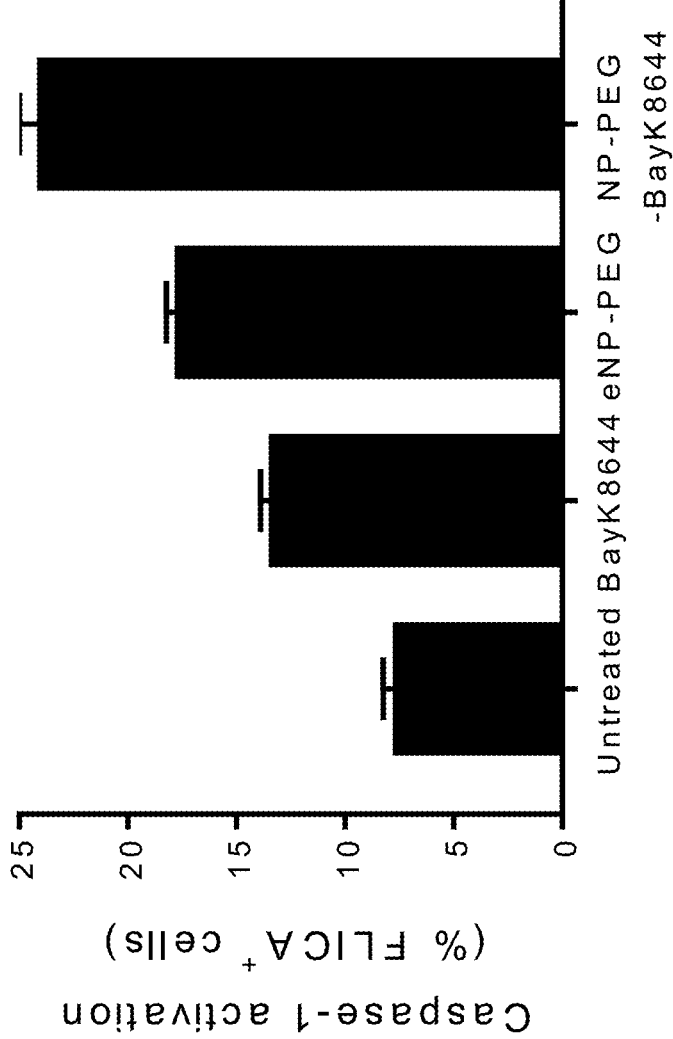

NP-PEG-BayK8664 were more effective than eNP-PEG and BayK8644 in inducing Caspase-1 activation in DCs (FIGS. 3I-J). Thus, NP-PEG-BayK8644 trigger inflammasome activation in DCs while preventing inhibition of antigen cross-presentation by (+)-BayK8644.

FIG. 3I, depicts Inflammasome activation studied in WT BMDCs treated as in FIG. 3H. This was performed by assessing Caspase-1 quantification by Flow cytometry using the FLICA-1 reagent. Representative dot plots are shown for the FLICA quantification by flow cytometry. One experiment representative of five is shown.

FIG. 3J A pool of the five experiments commented in FIG. 3I is shown.

Therapeutic Treatment with (+)-BayK8644 Encapsulated in Chitosan NPs Increases Survival and Retards Tumor Growth in a Tmem176b-Dependent Manner.

FIG. 4A-G depicts that the therapeutic treatment with (+)-BayK8644 encapsulated in chitosan nanoparticles (NP-PEG-BayK8644) increases mice survival and reduces tumor growth compared with empty nanoparticles (eNP-PEG).

WT and Tmem176b$^{-/-}$ animals were inoculated with EG7 tumors. Once tumors reached 25 mm$^2$, animals were i.t. injected with 70×10$^{-9}$ moles of (+)-BayK8644, NP-PEG-BayK8644 or eNP-PEG. Treatments were repeated every two days reaching a total of five injections. Mice were euthanized when the longer diameter reached tumors reached >200 mm.

Having shown that NP-PEG-BayK8644 do not inhibit antigen cross-presentation while still triggering inflammasome activation, we then studied whether those NPs may control tumor growth in vivo in a therapeutic setting. We had shown that although (+)-BayK8644 injected i.p before tumor establishment controlled its growth (preventive protocol), it failed to do so in animals with established tumors (therapeutic protocol) (15).

Figure 4A:
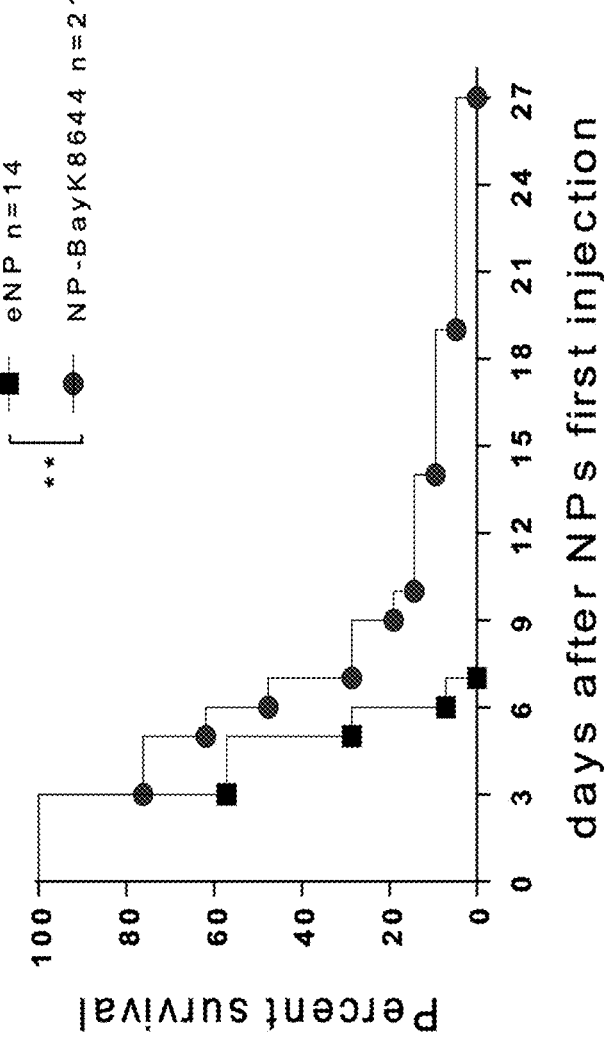
FIG. 4A-G. Therapeutic treatment with BayK8644 encapsulated in chitosan nanoparticles (NP-PEG-BayK8644) increases mice survival and reduces tumor growth compared with empty nanoparticles (eNP-PEG).

To evaluate the therapeutic efficacy of NPBayK8644, in vivo studies were carried out in WT mice carrying established EG7 tumors. We observed that intratumoral injection of NPBayK8644 significantly improved mouse survival and controlled tumor growth as compared to animals injected with eNPs (FIG. 4A, 4D). FIG. 4A depicts mouse survival of WT mice injected with NP-PEG-BayK8644 or eNP-PEG. **p<0.01. Log-rank (Mantel-Cox) Test; and FIG. 4D depicts tumor growth follow up in WT mice injected with NP-PEG-BayK8644 or eNP-PEG.

Figure 4B:
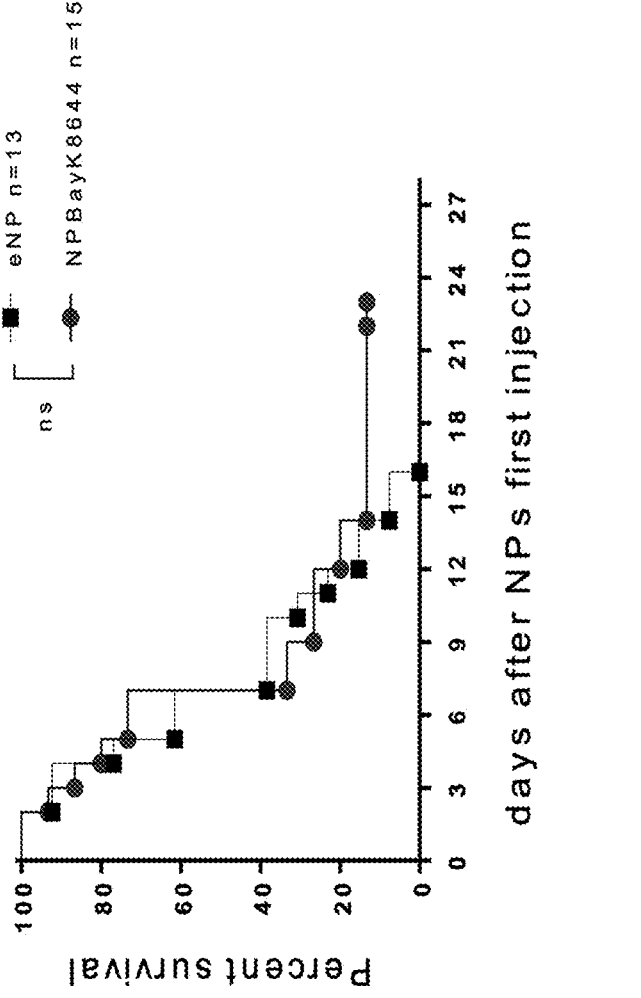
Figure 4C:
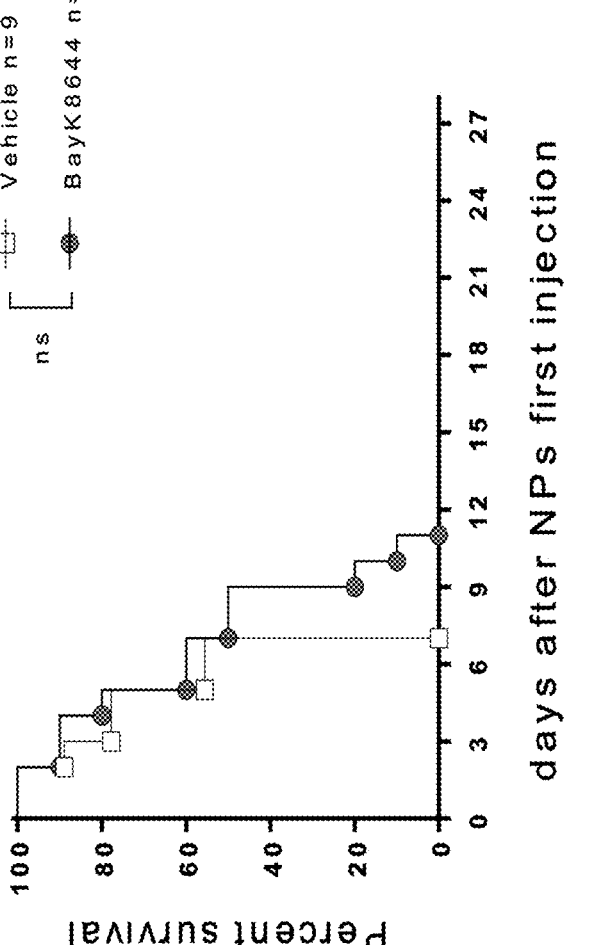
Figure 4D:
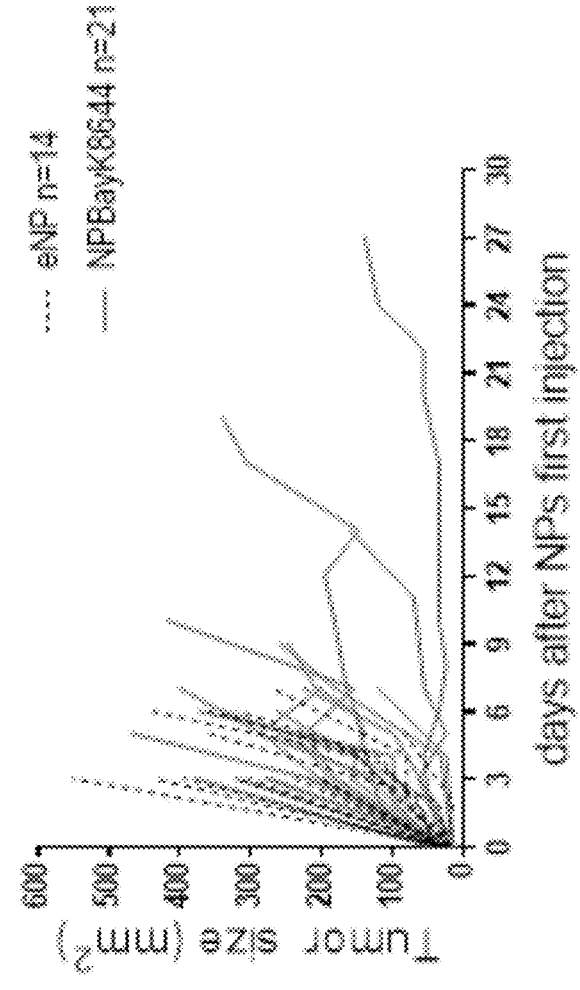
Figure 4E:
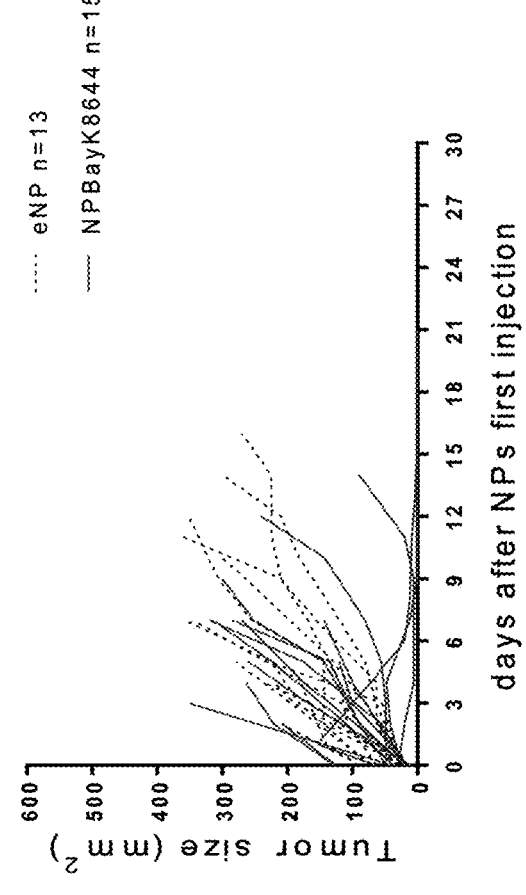

In contrast, when Tmem176b$^{-/-}$ animals were treated with NP-PEG-BayK8644 or eNP, we found no difference in mouse survival nor tumor growth in those conditions (FIG. 4B, 4E). FIG. 4B displays mouse survival of Tmem176b$^{-/-}$ injected with NP-PEG-BayK8644 or eNP-PEG. ns=not significant. Log-rank (Mantel-Cox) Test; and FIG. 4E displays tumor growth follow up in Tmem176b–/– injected with NP-PEG-BayK8644 or eNP-PEG.

Figure 4F:
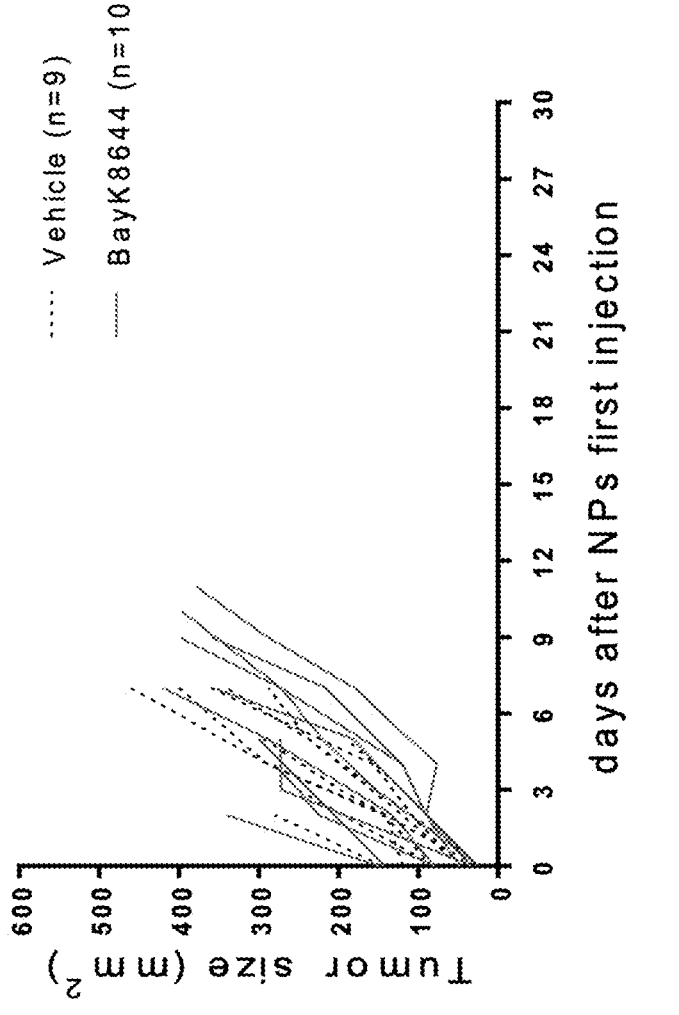

Thus, NPBayK8644 control tumor growth through a Tmem176b-dependent mechanism. Additionally, intratumoral injection of (+)-BayK8644 also failed to control tumor growth and improve mouse survival in comparison to vehicle-treated animals (FIG. 4C, 4F).

FIG. 4C displays mouse survival of WT mice injected with vehicle control or (+)-BayK8644. ns=not significant. Log-rank (Mantel-Cox) Test; and FIG. 4E displays Tumor growth follow up in Tmem176b$^{-/-}$ injected with NP-PEG-BayK8644 or eNP-PEG.

Figure 4G:
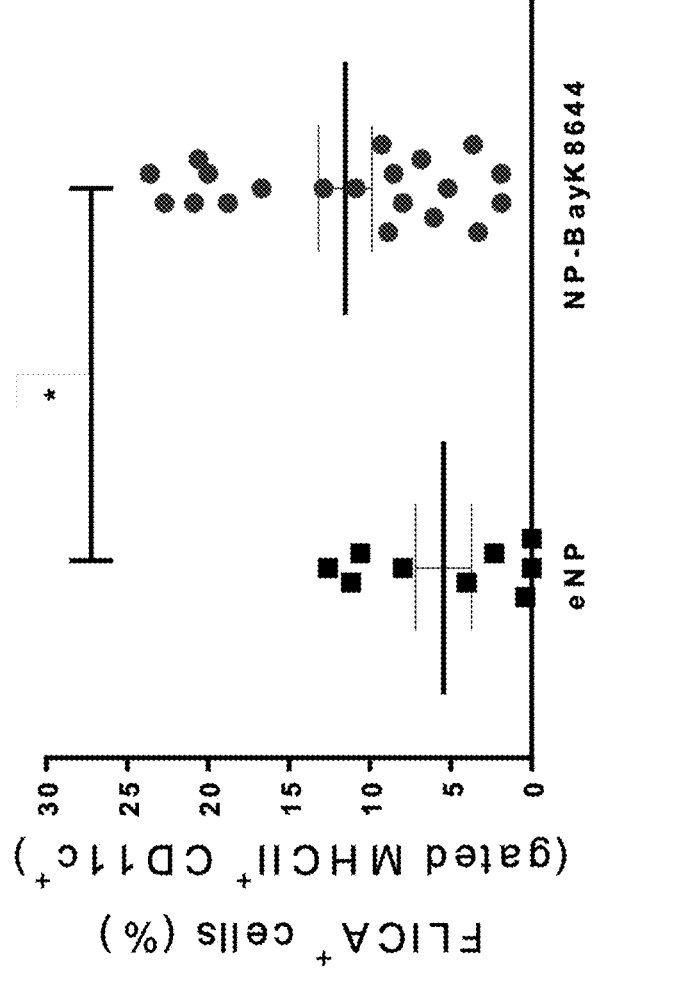

To further understand how NP-PEG-BayK8644 may control tumor growth, we assessed inflammasome activation in the tumor-draining lymph nodes (TDLN) of animals treated with NPBayK8644 or eNP. In fact, we had reported that i.p BayK8644 was associated with increased Caspase-1 activation in the TDLN and controls tumor growth in a Casp1/11-dependent manner (15). Indeed, we observed that NP- PEG-BayK8644 induced higher percentages of Caspase-1$^+$ DCs in the TDLN than eNP-PEG (FIG. 4G). Moreover, the anti-tumoral effect of NP-PEG-BayK8644 was inflammasome-dependent, since it was abrogated in Casp1/11$^{-/-}$ mice (FIG. 4H).

FIG. 4G depicts percentage of FLICA-1 (Active Caspase-1) positive cells within CD11c+MHC+ conventional DCs in the TDLN 15 days after tumor cell inoculation in WT animals i.t. injected with eNP-PEG or NP-PEG-BayK8644. *p<0.05, Student's t test.

Increased Tumor Infiltration by Total and Tumor-Specific CD8$^+$ T Cells is Associated with Tumor Control in NP-PEG-BayK8644-Treated Animals:

FIG. 5A-I shows that tumor control in NP-PEG-BayK8644-treated mice is associated with tumor cell infiltration by CD8$^+$ T cells.

WT mice were subcutaneously injected with $5.0 \times 10^5$ cell line E.G7-OVA. (+)-BayK8644, eNP-PEG or NP-PEG-BayK8644 were i.t injected every 2 days when tumors size reached 25 mm$^2$. CD8$^+$ T cells were studied in cellular suspensions from tumors and TDLNs harvested at 24 hs after the third NP or (+)-BayK8644 injection from the indicated groups. Animals from three experiments are shown. Absolute numbers are expressed by $1 \times 10^5$ tumor cells (V$\beta$12$^+$ cells). When indicated, NP-PEG-BayK8644-treated animals were classified as responders if at the resection time their tumor sized <100 mm$^2$ and as progressors if they sized >100 mm$^2$.

Figure 5A:
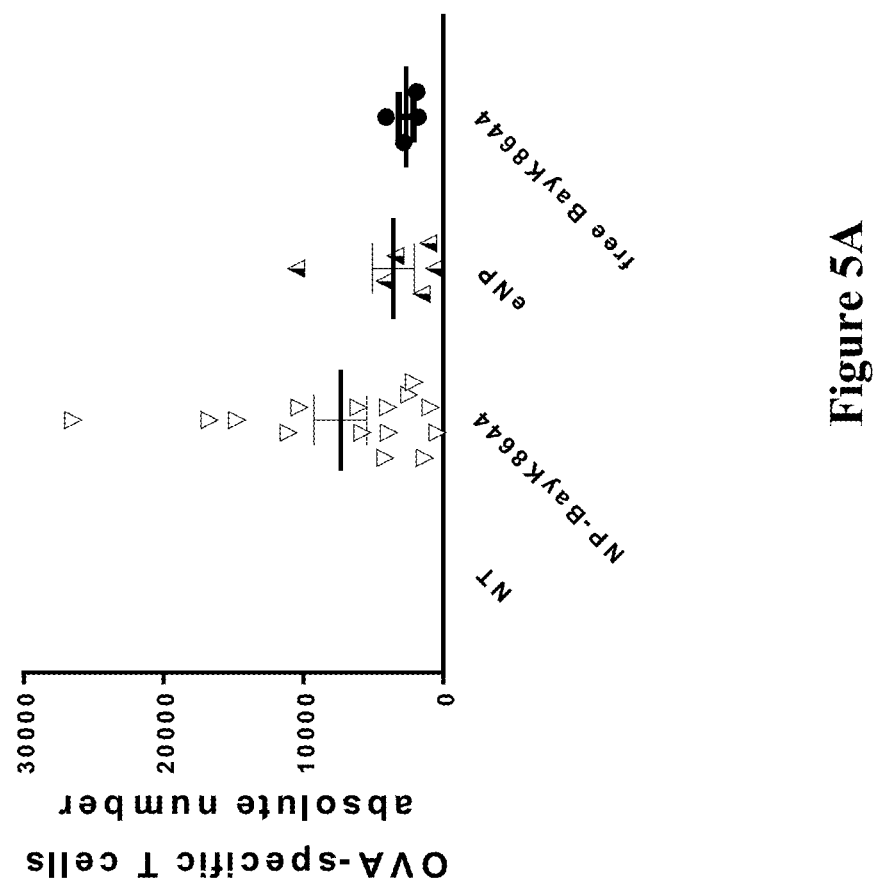
FIG. 5A-L. Tumor control in NP-PEG-BayK8644-treated mice is associated with tumor cell infiltration by CD8$^+$ T cells.
Figure 5B:
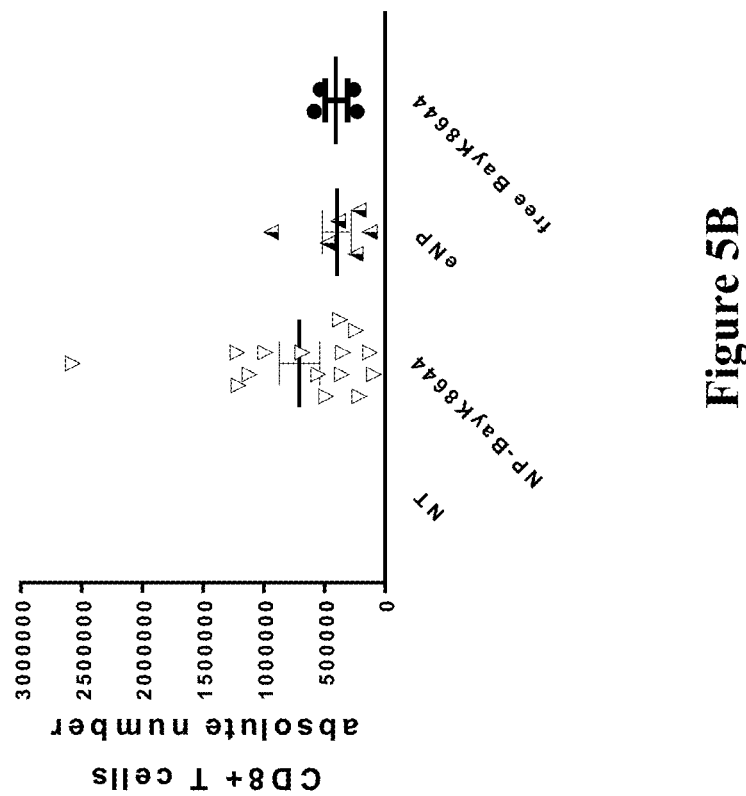
Figure 5C:
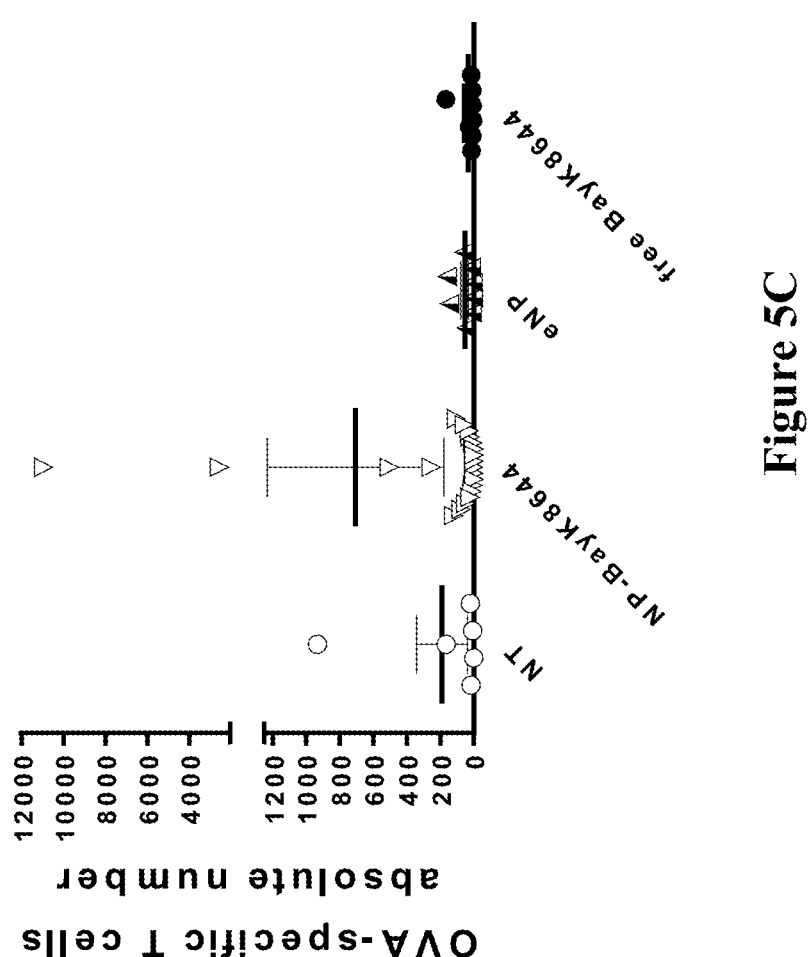
Figure 5D:
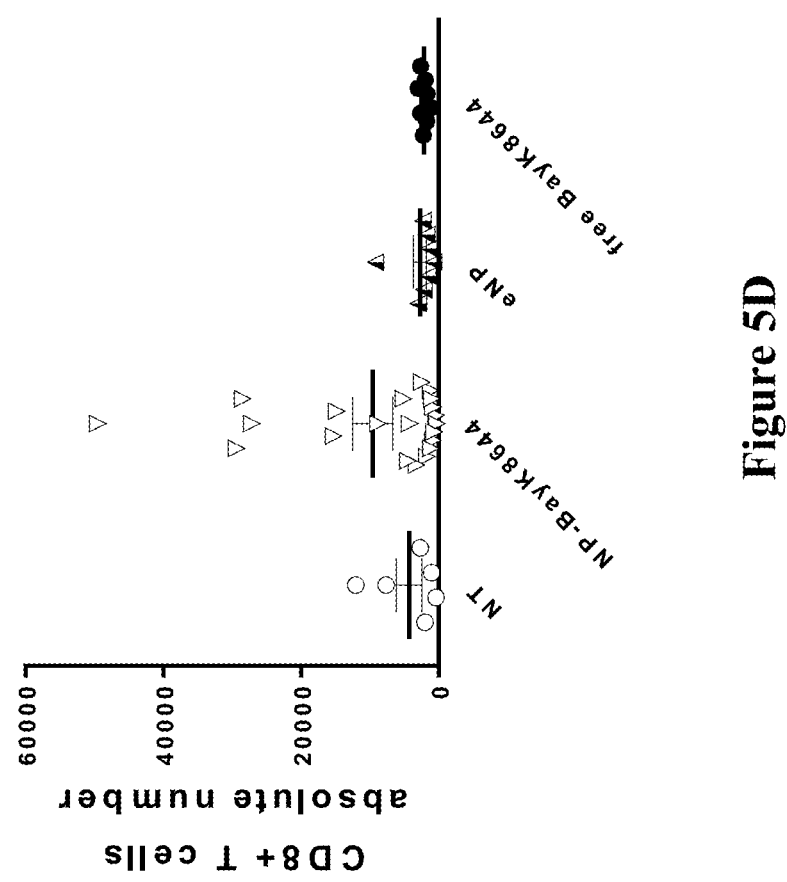

We then speculated that, in addition to its capacity to trigger inflammasome activation, preventing antigen cross-presentation inhibition by (+)-BayK8644 may enhance the anti-tumoral efficacy of NP-PEG-BayK8644. Anti-tumoral CD8$^+$ T cells are primed in the TDLN through the cross-presentation pathway. We therefore studied CD8$^+$ T cells by flow cytometry in the TDLN form EG7 tumors-bearing animals treated with (+)-BayK8644, eNP-PEG or NP-PEG-BayK8644. According to our hypothesis, absolute numbers of tumor-specific and total CD8$^+$ T cells were increased in the TDLN from NP-PEG-BayK8644 mice in comparison with (+)-BayK8644 and eNP-treated animals, although statistical significance was not reached (FIG. 5A-B). FIG. 5A depicts absolute numbers of OVA-specific CD8$^+$ T cells in tumors; and FIG. 5B depicts absolute numbers of total CD8$^+$ T cells in tumors. A similar trend was found in the tumor microenvironment for absolute numbers of total and tumor-specific (FIG. 5C-D) CD8$^+$ T cells, when comparing the three therapeutic groups. FIG. 5C illustrates absolute numbers of OVA-specific CD8$^+$ T cells in tumors; and FIG. 5D, illustrates absolute numbers of total CD8$^+$ T cells in tumors.

Figure 5E:
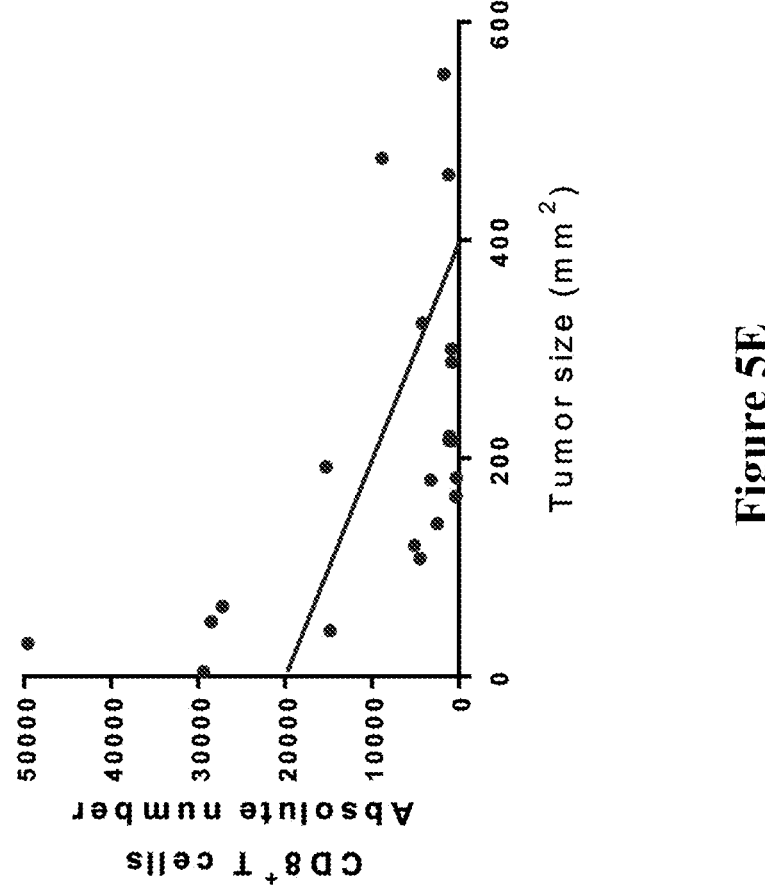
Figure 5F:
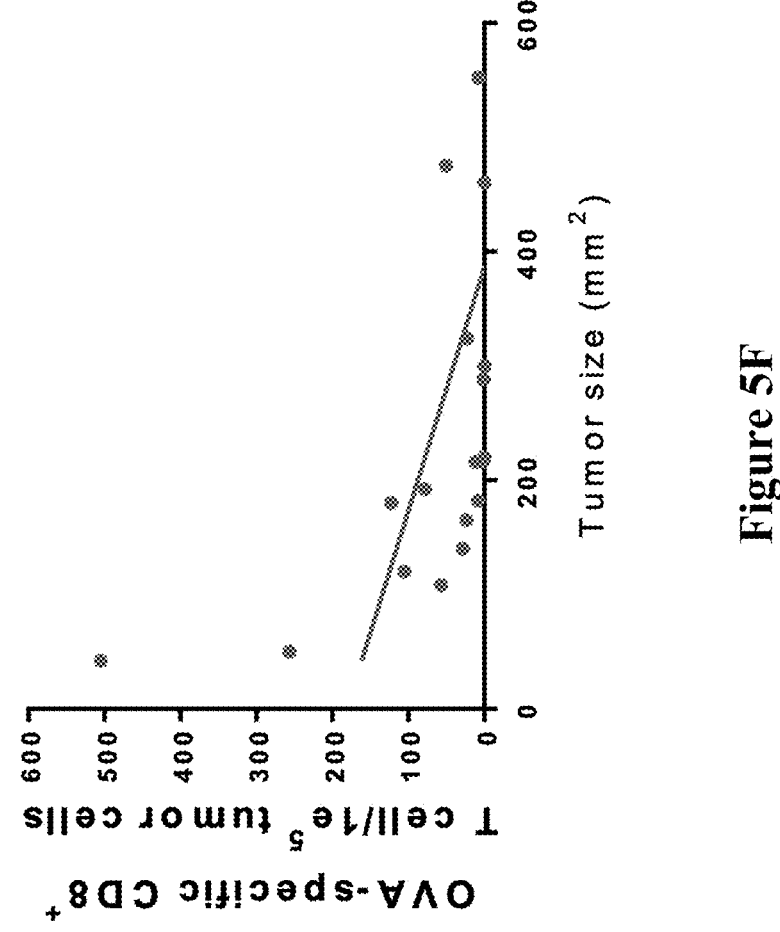

We did find a significant positive correlation between the size of tumors and the absolute numbers of total (FIG. 5E) and tumor-specific (FIG. 5F) tumor-infiltrating CD8$^+$ T cells within the NP-PEG-BayK8644-treated group. FIG. 5E shows a correlation study between the tumor-infiltrating total OVA-specific CD8$^+$ T cell absolute numbers and tumor size (mm$^2$). Correlation test. FIG. 5F shows a correlation study between the tumor-infiltrating CD8$^+$ T cell absolute numbers and tumor size (mm$^2$). Correlation test.

Figure 5G:
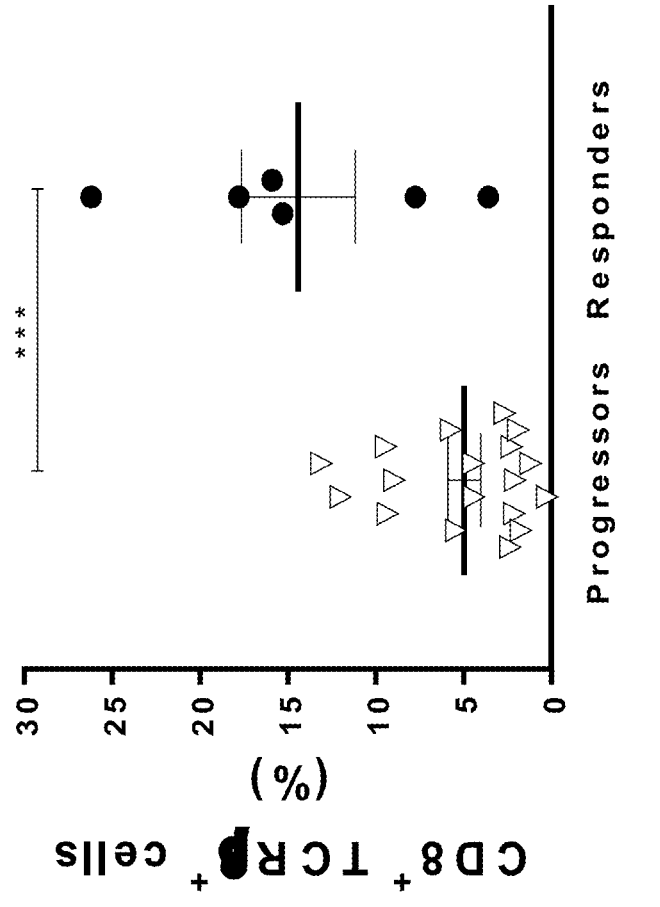
Figure 5H:
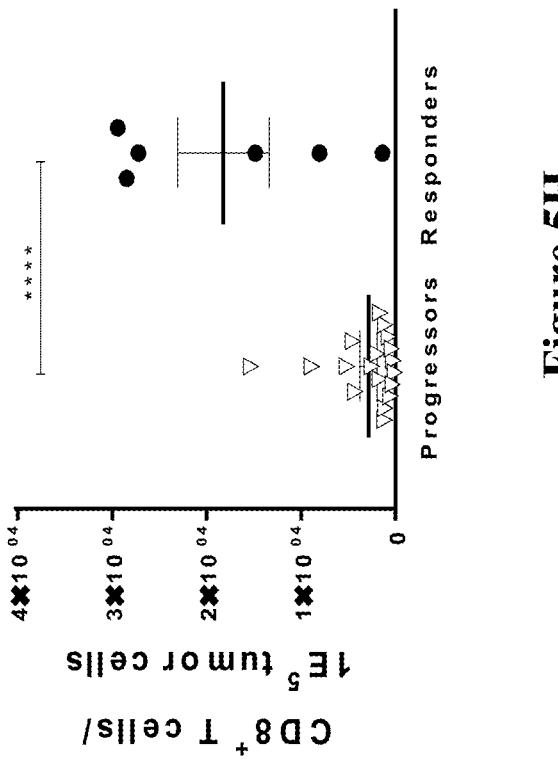
Figure 5I:
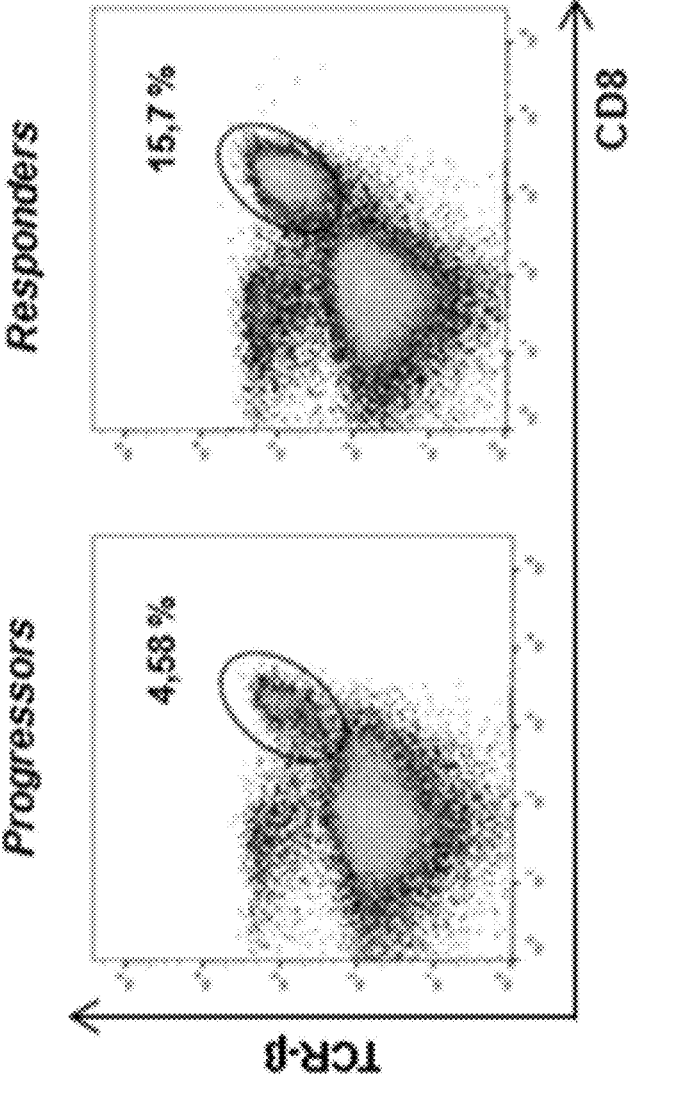

Accordingly, we observed a significant increase in the percentage and absolute number of intratumoral total CD8$^+$ T cells in animals controlling tumor growth (responders) versus progressors within the NP-PEG-BayK8644-treated group (FIG. 5G-I).

FIG. 5G depicts relative frequency of total CD8$^+$ T cells among V$\beta$12$^-$ cells in tumors of NP-PEG-BayK8644-treated mice comparing progressor and responder animals. * p<0.001, Student's t test. FIG. 5H depicts Absolute numbers of total CD8$^+$ T cells among V$\beta$12$^-$ cells in tumors of NP-PEG-BayK8644-treated mice comparing progressor and responder animals. * p<0.001, Student's t test. FIG. 5I depicts Representative flow cytometry dot plots of total and OVA-specific CD8$^+$ T cells in tumors of NP-PEG-BayK8644-treated mice comparing progressor and responder animals.

Figure 5J:
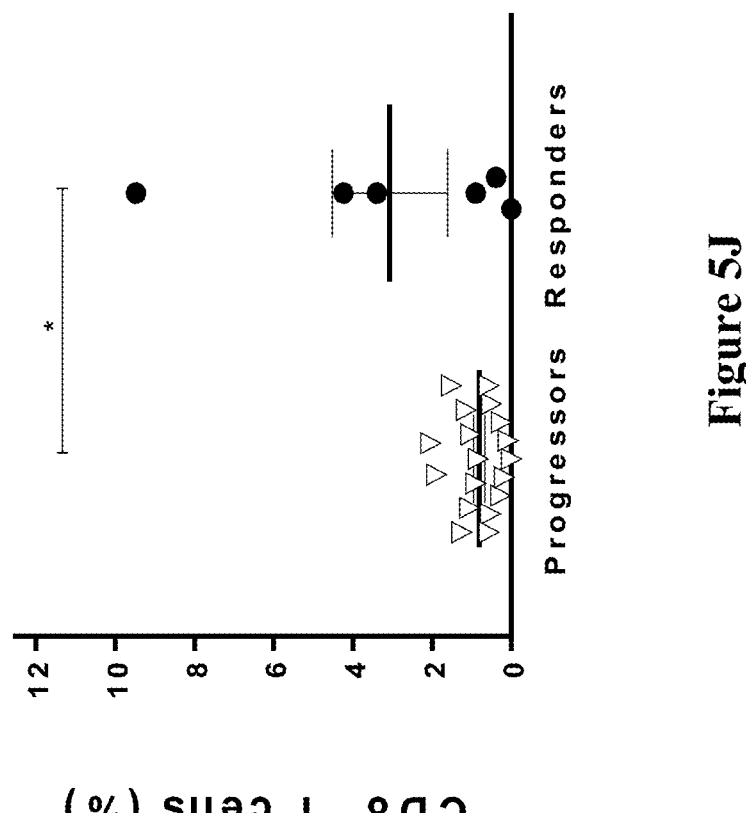

Similar results were found when analyzing intratumoral tumor-specific CD8$^+$ T cells (FIG. 5J, K, L). The analysis of CD8$^+$ T cells in the TDLN and tumor microenvironment therefore supports a role for preserved antigen cross-presentation in the anti-tumoral properties of NP-PEG-BayK8644.

FIG. 5J illustrates the relative frequency of OVA-specific CD8$^+$ T cells among V$\beta$12$^-$ cells in tumors of NP-PEG-BayK8644-treated mice comparing progressor and responder animals. * p<0.05, Student's t test.

Figure 5K:
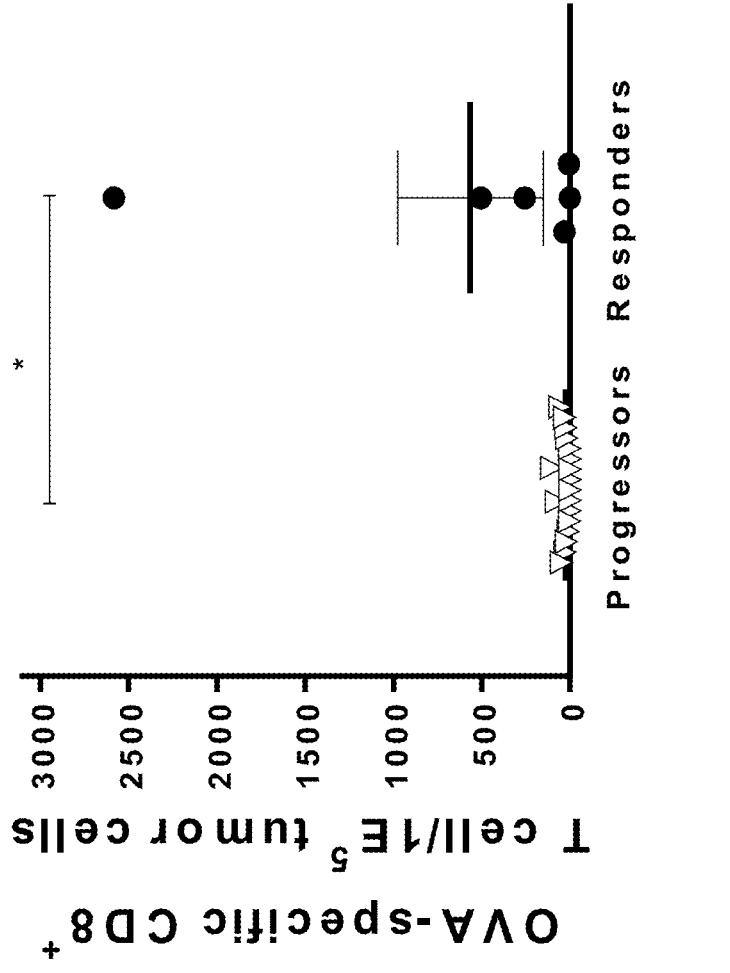

FIG. 5K illustrates absolute numbers of OVA-specific CD8$^+$ T cells among V$\beta$12$^-$ cells in tumors of NP-PEG-BayK8644-treated mice comparing progressor and responder animals. *** p<0.05, Student's t test.

Figure 5L:
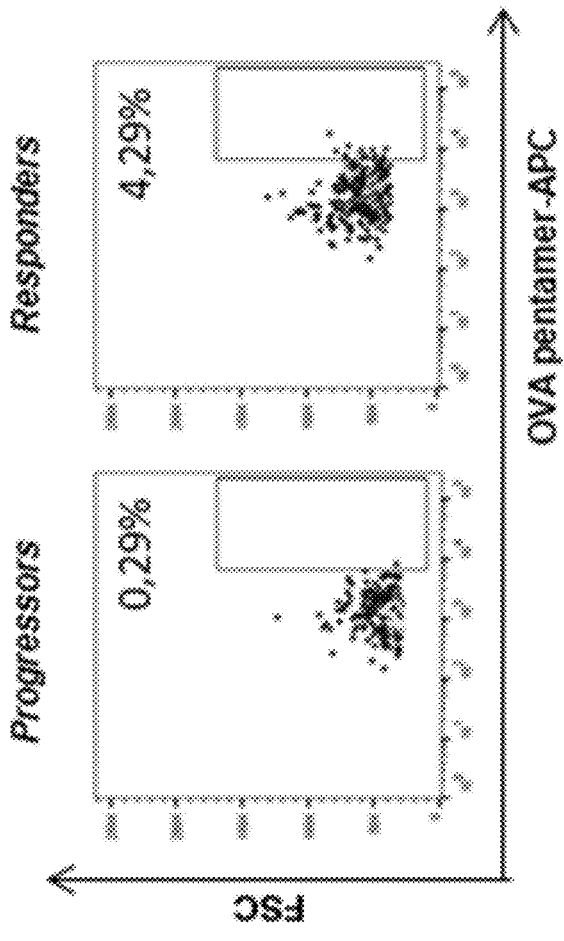

FIG. 5L illustrates representative dot plots.

Summary and Discussion: High TMEM176A/B expression has been associated with diminished overall survival in different human tumors, suggesting that it is a potential pharmacological target to control cancer progression (15, 17,18). (+)-BayK8644 triggers inflammasome and CD8$^+$ T cell-dependent anti-tumoral immune responses leading to tumor control in preventive but not in therapeutic protocols (15). The current invention discloses that formulating the TMEM176A/B inhibitor (+)-BayK8644 in chitosan nanoparticles prevents inhibition of antigen cross-presentation while strongly triggers inflammasome activation. This approach improves the anti-tumoral efficacy of the compound, allowing the control of established tumors in mice. Thus, a nanotechnology-based formulation was key to solve a biological problem such as inhibition of cross-presentation by (+)-BayK8644.

Understanding the mechanisms by which NP-PEG-BayK8644 control tumor growth is key to develop pharmacodynamic biomarkers which might help to determine which patients may respond to this approach in translational settings. Rational combination of therapies may also arise through this approach. Nevertheless, future work should study whether, as observed with (+)-BayK8644, NP-PEG-BayK8644 therapy may also be associated with increased CD4$^+$ RorgT$^+$ T cells and IL-17A production (5,15).

In summary, NPs are promising strategies for the controlled release of drugs, particularly in oncology (36). Although chitosan is considered a safe polymer, variations in origin, composition and molecular weight among other parameters have complicated the translational pathway of chitosan nanoparticles (37). Our study adds proof of concept of the reinforced anti-tumoral properties of (+)-BayK8644 through its encapsulation in nanoparticles. Further research will need to determine whether encapsulation of the compound in NPs of other materials will give similar results in preclinical models. The mechanisms studied here reveal that independently of the material used, (+)-BayK8644 should not be released at early time points after NP internalization to avoid inhibition of cross-presentation.

We have previously shown that its pharmacological blockade is not associated with toxicities in mice (15), though further toxicological studies in larger species are needed to position (+)-BayK8644 as a drug candidate. Additionally, immune-related adverse events triggered by TMEM176A/B inhibition remains to be determined. Nevertheless, we know that Tmem176b$^{-/-}$ mice do not suffer from spontaneous autoimmune disease (8,15).

Triggering inflammation to improve anti-tumoral immune responses and improve cancer immunotherapy is a matter of intense research (6,38). Specifically, intratumoral injection of inflammogenic NPs have shown promising results to control tumor growth. β-cyclodextrin nanoparticles loaded with the TLR-7 and TLR-8 agonist R848 sensitized the mouse colon tumors MC38 to anti-PD-1 therapy by polarizing tumor-associated macrophages to an M1 phenotype (39). The use of NPs has also been reported to trigger anti-tumoral immune responses in a STING (Stimulator of Interferon genes; TMEM173)-dependent manner. Tumoral antigens encapsulated in synthetic polymeric nanoparticles led to tumor control in mouse melanoma and colon cancer models through mechanisms involving STING (40). Moreover, endosomolytic polymersomes designed for the cytosolic delivery of STING agonists (cGAMP) improved the anti-tumoral therapeutic efficacy of the dinucleotides (41). In a different approach, endosomal disruption in DCs using polymer NPs loaded with tumoral peptides led to effective inhibition of tumor growth in mouse melanoma through mechanisms involving cross-presentation and NLRP3 inflammasome activation (42). Thus, combining STING agonists with TMEM176B inhibitors in a rationally designed NP that also allows the cross-presentation pathway to occur might result in strong inflammatory stimuli to trigger tumor immunity.

In conclusion, here we show that blocking the inflammasome inhibitor TMEM176B with NPs controls tumor growth in a Tmem176b, inflammasome and CD8$^+$ T cell-dependent manner. The nanotechnological formulation of (+)-BayK8644 allowed us to trigger inflammasome activation in the TDLN while avoiding inhibition of the cross-presentation pathway. Nevertheless, further toxicological studies are needed to translate this approach into clinical settings.

REFERENCES

1. Ribas A, Wolchok J D. Cancer immunotherapy using checkpoint blockade. Science. 2018; 359:1350-5.
2. Benci J L, Xu B, Qiu Y, Wu T J, Dada H, Twyman-Saint Victor C, et al. Tumor Interferon Signaling Regulates a Multigenic Resistance Program to Immune Checkpoint Blockade. Cell. 2016; 167:1540-1554.e12.
3. Pitt J M, Vétizou M, Daillère R, Roberti M P, Yamazaki T, Routy B, et al. Resistance Mechanisms to Immune-Checkpoint Blockade in Cancer: Tumor-Intrinsic and -Extrinsic Factors. Immunity. 2016; 44:1255-69.
4. Syn N L, Teng M W L, Mok T S K, Soo R A. De-novo and acquired resistance to immune checkpoint targeting. The Lancet Oncology. 2017; 18:e731-41.
5. Segovia M, Russo S, Girotti M R, Rabinovich G A, Hill M. Role of inflammasome activation in tumor immunity triggered by immune checkpoint blockers. Clin Exp Immunol. 2020; 200:155-62.
6. Hill M, Segovia M, Russo S, Girotti M, Rabinovich G A. The Paradoxical Roles of Inflammation during PD-1 Blockade in Cancer. Trends Immunol. 2020; 41:982-93.
7. Freeman T L, Swartz T H. Targeting the NLRP3 Inflammasome in Severe COVID-19. Front Immunol. 2020; 11:1518.
8. Segovia M, Louvet C, Charnet P, Savina A, Tilly G, Gautreau L, et al. Autologous Dendritic Cells Prolong Allograft Survival Through Tmem176b-Dependent Anti-gen Cross-Presentation: Immunoregulatory Mechanisms of Autologous DCs. American Journal of Transplantation. 2014; 14:1021-31.
9. Eon Kuek L, Leffler M, Mackay G A, Hulett M D. The MS4A family: counting past 1, 2 and 3. Immunol Cell Biol. 2016; 94:11-23.
10. Louvet C, Chiffoleau E, Heslan M, Tesson L, Heslan J-M, Brion R, et al. Identification of a New Member of the CD20/FcepsilonRIbeta Family Overexpressed in Tolerated Allografts. American Journal of Transplantation. 2005; 5:2143-53.
11. Condamine T, Le Texier L, Howie D, Lavault A, Hill M, Halary F, et al. Tmem176B and Tmem176A are associated with the immature state of dendritic cells. J Leukoc Biol. 2010; 88:507-15.
12. Villani A-C, Satija R, Reynolds G, Sarkizova S, Shekhar K, Fletcher J, et al. Single-cell RNA-seq reveals new types of human blood dendritic cells, monocytes, and progenitors. Science. 2017; 356:eaah4573.
13. Bourdely P, Anselmi G, Vaivode K, Ramos R N, Missolo-Koussou Y, Hidalgo S, et al. Transcriptional and Functional Analysis of C D 1 c+ Human Dendritic Cells Identifies a CD163+ Subset Priming CD8+CD103+ T Cells. Immunity. 2020; 53:335-352.e8.
14. Brown C C, Gudjonson H, Pritykin Y, Deep D, Lavallée V-P, Mendoza A, et al. Transcriptional Basis of Mouse and Human Dendritic Cell Heterogeneity. Cell. 2019; 179:846-863.e24.
15. Segovia M, Russo S, Jeldres M, Mahmoud Y D, Perez V, Duhalde M, et al. Targeting TMEM176B Enhances Antitumor Immunity and Augments the Efficacy of Immune Checkpoint Blockers by Unleashing Inflammasome Activation. Cancer Cell. 2019; 35:767-781.e6.
16. Rathinam V A K, Fitzgerald K A. Inflammasome Complexes: Emerging Mechanisms and Effector Functions. Cell. 2016; 165:792-800.
17. Liu Z, An H, Song P, Wang D, Li S, Chen K, et al. Potential targets of TMEM176A in the growth of glioblastoma cells. OTT. 2018; Volume 11:7763-75.
18. Sun L, Zhang Y, Zhang C. Distinct expression and prognostic value of MS4A in gastric cancer. Open Medicine. 2018; 13:178-88.
19. Theisen D J, Davidson J T, Briseño C G, Gargaro M, Lauron E J, Wang Q, et al. WDFY4 is required for cross-presentation in response to viral and tumor antigens. Science. 2018; 362:694-9.
20. Alloatti A, Rookhuizen D C, Joannas L, Carpier J-M, Iborra S, Magalhaes J G, et al. Critical role for Sec22b-dependent antigen cross-presentation in antitumor immunity. J Exp Med. 2017; 214:2231-41.
21. Savina A, Jancic C, Hugues S, Guermonprez P, Vargas P, Moura I C, et al. NOX2 controls phagosomal pH to regulate antigen processing during crosspresentation by dendritic cells. Cell. 2006; 126:205-18.
22. Jancic C, Savina A, Wasmeier C, Tolmachova T, El-Benna J, Dang P M-C, et al. Rab27a regulates phagosomal pH and NADPH oxidase recruitment to dendritic cell phagosomes. Nat Cell Biol. 2007; 9:367-78.
23. Savina A, Amigorena S. Phagocytosis and antigen presentation in dendritic cells. Immunol Rev. 2007; 219:143-56.
24. Savina A, Peres A, Cebrian I, Carmo N, Moita C, Hacohen N, et al. The Small GTPase Rac2 Controls Phagosomal Alkalinization and Antigen Crosspresentation Selectively in CD8+ Dendritic Cells. Immunity. 2009; 30:544-55.

25. Howland S W, Wittrup K D. Antigen Release Kinetics in the Phagosome Are Critical to Cross-Presentation Efficiency. The Journal of Immunology. 2008; 180:1576-83.

26. Lazaridou M, Christodoulou E, Nerantzaki M, Kostoglou M, Lambropoulou D, Katsarou A, et al. Formulation and In-Vitro Characterization of Chitosan-Nanoparticles Loaded with the Iron Chelator Deferoxamine Mesylate (DFO). Pharmaceutics. 2020; 12:238.

27. Cha J, Lee W B, Park C R, Cho Y W, Ahn C-H, Kwon I C. Preparation and characterization of cisplatin-incorporated chitosan hydrogels, microparticles, and nanoparticles. Macromol Res. 2006; 14:573-8.

28. Torrecilla D, Lozano M V., Lallana E, Neissa J I, Novoa-Carballal R, Vidal A, et al. Anti-tumor efficacy of chitosan-g-poly(ethylene glycol) nanocapsules containing docetaxel: Anti-TMEFF-2 functionalized nanocapsules vs. non-functionalized nanocapsules. European Journal of Pharmaceutics and Biopharmaceutics. Elsevier B.V.; 2013; 83:330-7.

29. Segovia M, Louvet C, Charnet P, Savina A, Tilly G, Gautreau L. Europe PMC Funders Group Autologous Dendritic Cells Prolong Allograft Survival Through Tmem176b-Dependent Antigen Cross-Presentation. 2015; 14:1021-31.

30. Segovia M, Cuturi M C, Hill M. Preparation of mouse bone marrow-derived dendritic cells with immunoregulatory properties. Methods in molecular biology (Clifton, NJ). United States; 2011; 677:161-8.

31. Livak K J, Schmittgen T D. Analysis of relative gene expression data using real-time quantitative PCR and the 2(-Delta Delta C(T)) Method. Methods (San Diego, Calif). United States; 2001; 25:402-8.

32. Karttunen J, Sanderson S, Shastri N. Detection of rare antigen-presenting cells by the lacZ T-cell activation assay suggests an expression cloning strategy for T-cell antigens. Proceedings of the National Academy of Sciences. 1992; 89:6020-4.

33. Howland S W, Wittrup K D. Antigen Release Kinetics in the Phagosome Are Critical to Cross-Presentation Efficiency. The Journal of Immunology. 2008; 180:1576-83.

34. Hoshyar N, Gray S, Han H, Bao G. The effect of nanoparticle size on in vivo pharmacokinetics and cellular interaction. Nanomedicine (London, England). 2016; 11:673-92.

35. Fan W, Yan W, Xu Z, Ni H. Formation mechanism of monodisperse, low molecular weight chitosan nanoparticles by ionic gelation technique. Colloids and surfaces B, Biointerfaces. Netherlands; 2012; 90:21-7.

36. Mitchell M J, Billingsley M M, Haley R M, Wechsler M E, Peppas N A, Langer R. Engineering precision nanoparticles for drug delivery. Nat Rev Drug Discov. 2021; 20:101-24.

37. Marques C, Som C, Schmutz M, Borges O, Borchard G. How the Lack of Chitosan Characterization Precludes Implementation of the Safe-by-Design Concept. Front Bioeng Biotechnol. 2020; 8:165.

38. Demaria O, Cornen S, Daeron M, Morel Y, Medzhitov R, Vivier E. Harnessing innate immunity in cancer therapy. Nature. 2019; 574:45-56.

39. Rodell C B, Arlauckas S P, Cuccarese M F, Garris C S, Li R, Ahmed M S, et al. TLR7/8-agonist-loaded nanoparticles promote the polarization of tumour-associated macrophages to enhance cancer immunotherapy. Nat Biomed Eng. 2018; 2:578-88.

40. Luo M, Wang H, Wang Z, Cai H, Lu Z, Li Y, et al. A STING-activating nanovaccine for cancer immunotherapy. Nature Nanotech. 2017; 12:648-54.

41. Shae D, Becker K W, Christov P, Yun D S, Lytton-Jean A K R, Sevimli S, et al. Endosomolytic polymersomes increase the activity of cyclic dinucleotide STING agonists to enhance cancer immunotherapy. Nat Nanotechnol. 2019; 14:269-78.

42. Gong N, Zhang Y, Teng X, Wang Y, Huo S, Qing G, et al. Proton-driven transformable nanovaccine for cancer immunotherapy. Nat Nanotechnol. 2020; 15:1053-64.

43. Mohammed, Munawar A., et al. "An overview of chitosan nanoparticles and its application in non-parenteral drug delivery." Pharmaceutics 9.4 (2017): 53.

44. Thomas, Gunter, Minn Chung, and Charles J. Cohen. "A dihydropyridine (Bay k 8644) that enhances calcium currents in guinea pig and calf myocardial cells. A new type of positive inotropic agent." Circulation research 56.1 (1985): 87-96.

45. Hamilton, Susan L., et al. "A comparison between the binding and electrophysiological effects of dihydropyridines on cardiac membranes." Molecular pharmacology 31.3 (1987): 221-231

The invention claimed is:

1. An anti-tumoral composition, for the treatment of neoplastic pathologies of malignant kind, wherein said composition comprises a TMEM176A/B inhibitor encapsulated in Chitosan nanoparticles, wherein said TMEM176A/B inhibitor is (+)BayK8644.

2. An anti-tumoral composition for the treatment of eg7 thymic lymphoma, wherein said composition comprises a TMEM176A/B inhibitor encapsulated in Chitosan nanoparticles, wherein said TMEM176A/B inhibitor is (+)BayK8644.

3. A method of treating neoplastic pathologies of malignant kind, wherein said method comprising the steps of administering to a subject a TMEM176A/B inhibitor formulated in Chitosan nanoparticles, wherein said TMEM176A/B inhibitor is (+)BayK8644.

* * * * *